United States Patent [19]

Falb et al.

[11] Patent Number: 5,807,708
[45] Date of Patent: Sep. 15, 1998

[54] CONSERVIN NUCLEIC ACID MOLECULES AND COMPOSITIONS

[75] Inventors: Dean A. Falb, Wellesley; Carlos J. Gimeno, Boston, both of Mass.

[73] Assignee: Millennium Pharmaceuticals, Inc., Cambridge, Mass.

[21] Appl. No.: 688,609

[22] Filed: Jul. 30, 1996

[51] Int. Cl.$^6$ .......................... C12N 15/18; C12N 15/09; C12N 5/10; C12N 15/63

[52] U.S. Cl. ...................... 435/69.1; 536/23.5; 536/23.1; 435/320.1; 435/325; 435/252.3; 435/254.11

[58] Field of Search .................... 536/23.5, 23.1; 435/320.1, 325, 252.3, 254.11, 69.1, 235.1; 424/450

[56] References Cited

U.S. PATENT DOCUMENTS

| | | | |
|---|---|---|---|
| 5,468,614 | 11/1995 | Fields et al. | 435/6 |
| 5,525,490 | 6/1996 | Erickson et al. | 435/29 |
| 5,593,879 | 1/1997 | Steller et al. | 435/240.1 |

FOREIGN PATENT DOCUMENTS

| | | |
|---|---|---|
| WO 92/05286 | 4/1992 | WIPO . |
| WO 94/10300 | 5/1994 | WIPO . |
| WO 96/02561A1 | 2/1996 | WIPO . |

OTHER PUBLICATIONS

Langer, R., "New Methods of Drug Delivery," *Science*, vol. 249, 1527–1532 (1990).
GenBank Accession No. W53857, Jun. 3, 1996.
GenBank Accession No. W46137, May 23, 1996.
GenBank Accession No. AA003882, Jul. 23, 1996.
GenBank Accession No. W75239, Jun. 20, 1996.
Bartel, P.L. et al."Using the two–hybrid system to detect protein–protein interactions", Hartley D.A., Practical Approach Series put out by New York State University, vol. 131 pp. 153–179.
Chien, C–T. et al. (1991) "The two hybrid system: A method to identify and clone genes for proteins that interact with a protein of interest", *Proc. Natl. Acad. Sci. USA* vol. 88:9578–9582.
Fields, S. and R. Sternglanz (1994), "The two–hybrid system: an assay for protein–protein interactions", *TIG* vol. 10:286–292.
Fritz, C.C. and M.R. Green (1992), "Fishing for partners", *Curr. Biol.* 8:403–405.
Guarente, L. (1993), "Strategies for the identification of interacting proteins", *Proc. Natl. Acad. Sci. USA* vol. 90:1639–1641.
Touchette, N. (1991), "New Approach Detects Protein Interactions In Vivo", *J. NIH Res.* 3:44,46.
Newmark, P. and Boswell, R., "The Mago Nashi Locus Encodes an Essential Product Required for Germ Plasm Assembly in Drosophila," *Development*, vol. 120, 1303–1313 (1994).
Wilson, R. et al., "2.2 Mb of Contiguous Nucleotide Sequence from Chromosome III of C. Elegans," *Nature*, vol. 368, 32–38 (1994).
GenBank™ Accession No. U89959 for *Arabidopsis thaliana*.

*Primary Examiner*—Stephen Walsh
*Assistant Examiner*—Claire M. Kaufman
*Attorney, Agent, or Firm*—Lahive & Cockfield, LLP

[57] ABSTRACT

The present invention relates to the discovery of novel conservin genes and polypeptides. Therapeutics, diagnostics and screening assays based on these molecules are also disclosed.

54 Claims, 4 Drawing Sheets

```
                                                                                      14
     GGCACGAGCGTCACTGCAAGGCGCCGGGGACACGTTGGCTGCGTTTT                                  42
     M   A   V   A   S   D   F   Y   L   R   Y   Y   V   G
CGGCGGGCTTCCCGGGTACAAAA ATG GCT GTG GCT AGC GAT TTC TAC CTG CGC TAC TAC GTA GGG

H   K   G   K   F   G   H   K   E   F   L   E   F   E   F   R   P   D   G   K   L   34
CAC AAG GGC AAG TTT GGG CAC GAG TTT CTG GAG TTC GAA TTT CGG CCG GAC GGA AAG CTT      102

R   Y   A   N   N   S   N   Y   K   N   D   V   M   I   R   K   E   A   Y   V       54
AGA TAT GCC AAC AAC AGC AAT TAC AAA AAT GAT GTG ATG ATC AGA AAA GAG GCT TAT GTG      162

H   K   S   V   M   E   E   L   K   R   I   I   D   D   S   E   I   T   K   E       74
CAC AAG AGT GTA ATG GAA GAA CTG AAG AGA ATT ATT GAT GAT AGT GAA ATT ACA AAA GAA      222

D   D   A   L   W   P   P   P   D   R   V   G   R   Q   E   L   E   I   V   I       94
GAT GAT GCT TTG TGG CCT CCC CCT GAT AGG GTT GGC CGA CAG GAG CTT GAA ATT GTA ATT      282

G   D   E   H   I   S   F   T   T   S   K   I   G   S   L   I   D   V   N   Q      114
GGA GAT GAG CAC ATA TCT TTT ACC ACA TCA AAA ATA GGT TCT CTT ATT GAT GTA AAT CAG      342

S   K   D   P   E   G   L   R   V   F   Y   Y   L   V   Q   D   L   K   C   L      134
TCA AAG GAT CCT GAA GGC CTT CGA GTA TTT TAC TAT TTG GTA CAA GAC TTG AAA TGT TTA      402

V   F   S   L   I   G   L   H   F   K   I   K   P   I   *                          148
GTT TTC AGT CTT ATT GGA TTA CAC TTC AAG ATT AAA CCA ATT TAA ATTGTATGTTTTCAGGCTG      444

TTTGTATATTTAATTAAGGATGGAGGGTTATTGTCATTTACAGTATTGGGGTTTTATGAATGTGAAGCAAACAA

AAAAAATTTGTATGTAAACTGAAAATAGAAAATACATTAGCAAGCTTAATGGTTATCCTTACTTGAGTCCACATGGT

TGGACAGTCCCCACACACATTAAATTCTGTAAATGAAAGCCACCTTTTGTTAAAAATTGCTCTAATAAACATACCCA

AATCCTGAAAAAAAAAAAAAAAAAAAAAAAAAAAAAAAAAAANAAAAAAAAAAAAAAAA
```

FIG. 1

```
                                                                                GGCACGAGGACGGGGCAGTGGGCTTGCT

M   E   S   D   F   Y   L   R   Y   Y   V                                                         11
              ATG GAG AGT GAC TTT TAT CTG CGT TAC TAC GTG                                                        33

G   H   K   G   K   F   G   H   E   F   L   E   F   E   R   P   D   G   K                                       31
GGG CAC AAG GGC AAG TTC GGC CAC GAG TTC CTG GAG TTT CGA CCG GAC GGG AAG                                          93

L   R   Y   A   N   N   S   N   Y   K   N   D   V   M   I   R   K   E   A   Y                                   51
TTA AGA TAT GCC AAC AAC AGC AAT TAC AAG AAT GAT GTC ATG ATC AGA AAA GAG GCT TAT                                  153

V   H   K   S   V   M   E   E   L   K   R   I   I   D   D   S   E   I   T   K                                   71
GTA CAT AAA AGC GTG ATG GAG GAA CTG AAG AGA ATA ATT GAC GAC AGT GAA ATT ACC AAA                                  213

E   D   D   A   L   W   P   P   P   P   D   R   V   G   R   Q   E   L   I   V                                   91
GAG GAT GAT GCA TTG TGG CCT CCT CCT CCT GAC CGA GTG GGC CGG CAG GAG CTT ATC GTC                                  273

I   G   D   E   H   I   S   F   T   T   S   K   I   K   I   L   I   D   V   N                                   111
ATT GGA GAT GAA CAC ATT TCT TTT ACA ACA TCA AAA ATT GGT TCC CTT ATT GAT GTC AAT                                  333

Q   S   K   D   P   E   G   L   R   V   F   Y   Y   L   V   Q   D   L   K   C                                   131
CAA TCC AAG GAT CCA GAA GGC TTA CGA GTA TTT TAT CTT GTC CAG GAC CTG AAG TGT                                      393

L   V   F   S   L   I   G   L   H   F   K   I   K   P   I   *                                                   146
TTG GTC TTC AGT CTT ATT GGA TTA CAC TTC AAG ATT AAA CCA ATC TAG ACTGAATATTGTGT                                   438

GGACATGGGGGTGGGTGGGAGTACAAAATTTGTGTATATCAGGCAGTATTCNTCTATGAACTA
```

FIG.2

```
mn_CDS    ATGTCCACGG---AGGACTTTTACCTACGCTACTACGTCGGACACAAGGGCAAGTTCGGG
tyhv012   ATGGCTGTGGCTAGCGATTCTACCTGCGCTACTACGTAGGGCACAAGGGCAAGTTTGGG
tyhv015   ATGGAGAG------TGACTTTTATCTGCGTTACTACGTGGGGCACAAGGGCAAGTTCGGC mn_CDS    CACGAATTCTTGGAGTTCGAGTTCCGGCCGGATGGCAAGCTGCGGTACGCCAACAACTCC
tyhv012   CACGAGTTTCTGGAGTTCGAGTTCCGGCCGGAGTTCGGCCGGAGAAAGCTTAGATATGCCAACAACAGC
tyhv015   CACGAGTTCCTGGAGTTTGAGTTCGACCGGAGTTTGAGCCGGGAAGTTAAGATATGCCAACAACAGC mn_CDS    AACTACAAGAACGACACCATGATCCGCAAGGAGGCCTTCGTCCACCAGTCCGTGATGGAA
tyhv012   AATTACAAAAATGATGTGATCAGAAAAGAGGCTTATGTGCACAAGAGTGTAATGGAA
tyhv015   AATTACAAGAATGATGTCATGATCAGAGAAAAGAGGCTTATGTACATAAAAGCTGATGGAG mn_CDS    GAACTGAAGCGAATCATCATCGACTCGGAGATCATGCAGGAGGACGATCTGCCCTGGCCG
tyhv012   GAACTGAAGAGAATTATTGATGACAGTGAATTACAAAAGAAGATGATGCTTTGTGGCCT
tyhv015   GAACTGAAGAGAATAATTGACGACAGTGAATTACCAAAGAGGATGATGCATTGTGGCCT mn_CDS    CCACCAGATCGCGTGGTCGACAGGAACTGGAGATCGTCATCGGAGACGAGCACATCTCG
tyhv012   CCCCCTGATAGGGTTGGCCGCACAGGAGCTTGAAATTGTAATTGGAGATGAGCACATATCT
tyhv015   CCTCCTGACCGAGTGGGCCGGCCGAGTGGGCCAGGAGCTTGAAATCGTCATTGGAGATGAACACATTTCT mn_CDS    TTCACCACCTCGAAAACGGGATCATTGGTGGACGTGAACCGGTCAAAAGATCCCGAGGGC
tyhv012   TTTACCACATCAAAAAATAGTTCTCTTATTGATGTAAATCAGTGAATCAAAGGATCCTGAAGGC
tyhv015   TTTACAACAACATCAAAAATTGGTTCCCTTATTGATGTCAATCCAAGGATCCAGAAGGC mn_CDS    CTGCGATGCTTTACTACCTGGTGCAGGATCTCAAGTGCCTGGTCTTCTCACTCATCGGC
tyhv012   CTTCGAGTATTTACTATTTGGTACAAGACTTGAAATGTTTAGTTTTCAGTCTTATTGGA
tyhv015   TTACGAGTATTTTTATTATCTGTCCAGGACCTGAAGTGTTTGGTGTTCTTCAGTCTTATTGGA mn_CDS    CTGCATTTCAAGATCAAGCCCATATAA
tyhv012   TTACACTTCAAGATTAAACCAATTTAA
tyhv015   TTACACTTCAAGATTAAACCAATCTAG
```

FIG. 3

```
Mago_nashi  M-STEDFYLRYYVGHKGKFGHEFLEFEFRPDGKLRYANNSNYKNDTMIRKEAFVHQSVME
tyhv012     MAVASDFYLRYYVGHKGKFGHEFLEFEFRPDGKLRYANNSNYKNDVMIRKEAYVHKSVME
tyhv015     M--ESDFYLRYYVGHKGKFGHEFLEFEFRPDGKLRYANNSNYKNDVMIRKEAYVHKSVME Mago_nashi  ELKRIIIDSEIMQEDDLPWPPPDRVGRQELEIVIGDEHISFTTSKTGSLVDVNRSKDPEG
tyhv012     ELKRIIDDSEITKEDDALWPPPDRVGRQELEIVIGDEHISFTTSKIGSLIDVNQSKDPEG
tyhv015     ELKRIIDDSEITKEDDALWPPPDRVGRQELEIVIGDEHISFTTSKIGSLIDVNQSKDPEG Mago_nashi  LRCFYYLVQDLKCLVFSLIGLHFKIKPI
tyhv012     LRVFYYLVQDLKCLVFSLIGLHFKIKPI
tyhv015     LRVFYYLVQDLKCLVFSLIGLHFKIKPI
```

FIG. 4

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 830 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 72..516

( x i ) SEQUENCE DESCRIPTION: SEQ ID NO:1:

```
GGCACGAGCG  TCACTGCAAG  GCGCCGGGGG  ACACGTTGGC  TGCGTTTTCG  GCGGGCTTCC         60

CGGGTACAAA A ATG GCT GTG GCT AGC GAT TTC TAC CTG CGC TAC TAC GTA            110
           Met Ala Val Ala Ser Asp Phe Tyr Leu Arg Tyr Tyr Val
             1               5                          10

GGG CAC AAG GGC AAG TTT GGG CAC GAG TTT CTG GAG TTC GAA TTT CGG            158
Gly His Lys Gly Lys Phe Gly His Glu Phe Leu Glu Phe Glu Phe Arg
         15                  20                  25

CCG GAC GGA AAG CTT AGA TAT GCC AAC AAC AGC AAT TAC AAA AAT GAT            206
Pro Asp Gly Lys Leu Arg Tyr Ala Asn Asn Ser Asn Tyr Lys Asn Asp
 30                  35                  40                  45

GTG ATG ATC AGA AAA GAG GCT TAT GTG CAC AAG AGT GTA ATG GAA GAA            254
Val Met Ile Arg Lys Glu Ala Tyr Val His Lys Ser Val Met Glu Glu
                 50                  55                  60

CTG AAG AGA ATT ATT GAT GAC AGT GAA ATT ACA AAA GAA GAT GAT GCT            302
Leu Lys Arg Ile Ile Asp Asp Ser Glu Ile Thr Lys Glu Asp Asp Ala
             65                  70                  75

TTG TGG CCT CCC CCT GAT AGG GTT GGC CGA CAG GAG CTT GAA ATT GTA            350
Leu Trp Pro Pro Pro Asp Arg Val Gly Arg Gln Glu Leu Glu Ile Val
         80                  85                  90

ATT GGA GAT GAG CAC ATA TCT TTT ACC ACA TCA AAA ATA GGT TCT CTT            398
Ile Gly Asp Glu His Ile Ser Phe Thr Thr Ser Lys Ile Gly Ser Leu
     95                  100                 105

ATT GAT GTA AAT CAG TCA AAG GAT CCT GAA GGC CTT CGA GTA TTT TAC            446
Ile Asp Val Asn Gln Ser Lys Asp Pro Glu Gly Leu Arg Val Phe Tyr
110                 115                 120                 125

TAT TTG GTA CAA GAC TTG AAA TGT TTA GTT TTC AGT CTT ATT GGA TTA            494
Tyr Leu Val Gln Asp Leu Lys Cys Leu Val Phe Ser Leu Ile Gly Leu
                 130                 135                 140

CAC TTC AAG ATT AAA CCA ATT T AAATTGTATG TTTTCAGGCT GTTTGTATAT             546
His Phe Lys Ile Lys Pro Ile
             145
```

```
TTAATTAAGG  GATGGGAGGG  GTTATTTGTC  ATTACAGTA   TTGGGGTTTT  TATGAATGTG     606

AAGCAAACAA  AAAAAATTTG  TATGTAAACT  GAAATAAGA   AAATACATTA  GCAAGCTTAA     666

TGGTTATCCT  TACTTGAGTC  CACATGGGTT  GGACAGTCCC  CACACACATT  AAATTCTGTA     726

AATGAAAGCC  ACCTTTTGTT  AAAAATTTGC  TCTAATAAAA  CATACCCAAA  TCCTGAAMAA     786

AAAAAAAAAA  AAAAAAAAA   AAAAAAANAA  AAAAAAAAA   AAAA                      830
```

( 2 ) INFORMATION FOR SEQ ID NO:2:

( i ) SEQUENCE CHARACTERISTICS:
        ( A ) LENGTH: 444 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
ATGGCTGTGG  CTAGCGATTT  CTACCTGCGC  TACTACGTAG  GGCACAAGGG  CAAGTTTGGG      60

CACGAGTTTC  TGGAGTTCGA  ATTTCGGCCG  GACGGAAAGC  TTAGATATGC  CAACAACAGC     120

AATTACAAAA  ATGATGTGAT  GATCAGAAAA  GAGGCTTATG  TGCACAAGAG  TGTAATGGAA     180

GAACTGAAGA  GAATTATTGA  TGACAGTGAA  ATTACAAAAG  AAGATGATGC  TTTGTGGCCT     240

CCCCCTGATA  GGGTTGGCCG  ACAGGAGCTT  GAAATTGTAA  TTGGAGATGA  GCACATATCT     300

TTTACCACAT  CAAAAATAGG  TTCTCTTATT  GATGTAAATC  AGTCAAAGGA  TCCTGAAGGC     360

CTTCGAGTAT  TTTACTATTT  GGTACAAGAC  TTGAAATGTT  TAGTTTTCAG  TCTTATTGGA     420

TTACACTTCA  AGATTAAACC  AATT                                              444
```

( 2 ) INFORMATION FOR SEQ ID NO:3:

( i ) SEQUENCE CHARACTERISTICS:
        ( A ) LENGTH: 148 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Ala  Val  Ala  Ser  Asp  Phe  Tyr  Leu  Arg  Tyr  Tyr  Val  Gly  His  Lys
 1              5                        10                           15

Gly  Lys  Phe  Gly  His  Glu  Phe  Leu  Glu  Phe  Glu  Phe  Arg  Pro  Asp  Gly
              20                        25                       30

Lys  Leu  Arg  Tyr  Ala  Asn  Asn  Ser  Asn  Tyr  Lys  Asn  Asp  Val  Met  Ile
              35                       40                        45

Arg  Lys  Glu  Ala  Tyr  Val  His  Lys  Ser  Val  Met  Glu  Glu  Leu  Lys  Arg
         50                       55                       60

Ile  Ile  Asp  Asp  Ser  Glu  Ile  Thr  Lys  Glu  Asp  Asp  Ala  Leu  Trp  Pro
 65                       70                       75                       80

Pro  Pro  Asp  Arg  Val  Gly  Arg  Gln  Glu  Leu  Glu  Ile  Val  Ile  Gly  Asp
                   85                       90                       95

Glu  His  Ile  Ser  Phe  Thr  Thr  Ser  Lys  Ile  Gly  Ser  Leu  Ile  Asp  Val
                  100                      105                      110

Asn  Gln  Ser  Lys  Asp  Pro  Glu  Gly  Leu  Arg  Val  Phe  Tyr  Tyr  Leu  Val
              115                      120                      125

Gln  Asp  Leu  Lys  Cys  Leu  Val  Phe  Ser  Leu  Ile  Gly  Leu  His  Phe  Lys
              130                      135                      140

Ile  Lys  Pro  Ile
```

145

( 2 ) INFORMATION FOR SEQ ID NO:4:

( i ) SEQUENCE CHARACTERISTICS:
        ( A ) LENGTH: 587 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 66..504

( x i ) SEQUENCE DESCRIPTION: SEQ ID NO:4:

```
GGCACGAGGA CGGCGGCAGT GCGGCTTGCT CTTGGAAGTT CAGGCTCGGT TGTCTTTTGG          60

GAGCC ATG GAG AGT GAC TTT TAT CTG CGT TAC TAC GTG GGG CAC AAG            107
      Met Glu Ser Asp Phe Tyr Leu Arg Tyr Tyr Val Gly His Lys
      1               5                   10

GGC AAG TTC GGC CAC GAG TTC CTG GAG TTT GAG TTT CGA CCG GAC GGG          155
Gly Lys Phe Gly His Glu Phe Leu Glu Phe Glu Phe Arg Pro Asp Gly
15              20                  25                  30

AAG TTA AGA TAT GCC AAC AAC AGC AAT TAC AAG AAT GAT GTC ATG ATC          203
Lys Leu Arg Tyr Ala Asn Asn Ser Asn Tyr Lys Asn Asp Val Met Ile
                35                  40                  45

AGA AAA GAG GCT TAT GTA CAT AAA AGC GTG ATG GAG GAA CTG AAG AGA          251
Arg Lys Glu Ala Tyr Val His Lys Ser Val Met Glu Glu Leu Lys Arg
            50                  55                  60

ATA ATT GAC GAC AGT GAA ATT ACC AAA GAG GAT GAT GCA TTG TGG CCT          299
Ile Ile Asp Asp Ser Glu Ile Thr Lys Glu Asp Asp Ala Leu Trp Pro
        65                  70                  75

CCT CCT GAC CGA GTG GGC CGG CAG GAG CTT GAA ATC GTC ATT GGA GAT          347
Pro Pro Asp Arg Val Gly Arg Gln Glu Leu Glu Ile Val Ile Gly Asp
    80                  85                  90

GAA CAC ATT TCT TTT ACA ACA TCA AAA ATT GGT TCC CTT ATT GAT GTC          395
Glu His Ile Ser Phe Thr Thr Ser Lys Ile Gly Ser Leu Ile Asp Val
95                  100                 105                 110

AAT CAA TCC AAG GAT CCA GAA GGC TTA CGA GTA TTT TAT TAT CTT GTC          443
Asn Gln Ser Lys Asp Pro Glu Gly Leu Arg Val Phe Tyr Tyr Leu Val
                115                 120                 125

CAG GAC CTG AAG TGT TTG GTC TTC AGT CTT ATT GGA TTA CAC TTC AAG          491
Gln Asp Leu Lys Cys Leu Val Phe Ser Leu Ile Gly Leu His Phe Lys
            130                 135                 140

ATT AAA CCA ATC T AGACTGAATA TTGGTGTGGA CATGGGGGGT GGGTGGGAGT            544
Ile Lys Pro Ile
            145

ACAAAATTTT GTGTATATCA GGGCAGTATT CNTCTATGAA CTA                          587
```

( 2 ) INFORMATION FOR SEQ ID NO:5:

( i ) SEQUENCE CHARACTERISTICS:
        ( A ) LENGTH: 438 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

```
ATGGAGAGTG ACTTTTATCT GCGTTACTAC GTGGGGCACA AGGGCAAGTT CGGCCACGAG          60

TTCCTGGAGT TTGAGTTTCG ACCGGACGGG AAGTTAAGAT ATGCCAACAA CAGCAATTAC         120
```

| | | | | | |
|---|---|---|---|---|---|
|AAGAATGATG|TCATGATCAG|AAAAGAGGCT|TATGTACATA|AAAGCGTGAT|GGAGGAACTG 180|
|AAGAGAATAA|TTGACGACAG|TGAAATTACC|AAAGAGGATG|ATGCATTGTG|GCCTCCTCCT 240|
|GACCGAGTGG|GCCGGCAGGA|GCTTGAAATC|GTCATTGGAG|ATGAACACAT|TTCTTTTACA 300|
|ACATCAAAAA|TTGGTTCCCT|TATTGATGTC|AATCAATCCA|AGGATCCAGA|AGGCTTACGA 360|
|GTATTTTATT|ATCTTGTCCA|GGACCTGAAG|TGTTTGGTCT|TCAGTCTTAT|TGGATTACAC 420|
|TTCAAGATTA|AACCAATC| | | |438|

( 2 ) INFORMATION FOR SEQ ID NO:6:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Glu  Ser  Asp  Phe  Tyr  Leu  Arg  Tyr  Tyr  Val  Gly  His  Lys  Gly  Lys
 1                    5                   10                       15

Phe  Gly  His  Glu  Phe  Leu  Glu  Phe  Glu  Phe  Arg  Pro  Asp  Gly  Lys  Leu
              20                        25                       30

Arg  Tyr  Ala  Asn  Asn  Ser  Asn  Tyr  Lys  Asn  Asp  Val  Met  Ile  Arg  Lys
              35                        40                       45

Glu  Ala  Tyr  Val  His  Lys  Ser  Val  Met  Glu  Glu  Leu  Lys  Arg  Ile  Ile
         50                   55                        60

Asp  Asp  Ser  Glu  Ile  Thr  Lys  Glu  Asp  Asp  Ala  Leu  Trp  Pro  Pro  Pro
65                        70                        75                       80

Asp  Arg  Val  Gly  Arg  Gln  Glu  Leu  Glu  Ile  Val  Ile  Gly  Asp  Glu  His
                   85                        90                       95

Ile  Ser  Phe  Thr  Thr  Ser  Lys  Ile  Gly  Ser  Leu  Ile  Asp  Val  Asn  Gln
                  100                       105                      110

Ser  Lys  Asp  Pro  Glu  Gly  Leu  Arg  Val  Phe  Tyr  Tyr  Leu  Val  Gln  Asp
              115                       120                      125

Leu  Lys  Cys  Leu  Val  Phe  Ser  Leu  Ile  Gly  Leu  His  Phe  Lys  Ile  Lys
              130                       135                      140

Pro  Ile
145
```

( 2 ) INFORMATION FOR SEQ ID NO:7:

( i ) SEQUENCE CHARACTERISTICS:
        ( A ) LENGTH: 444 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
|ATGTCCACGG|AGGACTTTTA|CCTACGCTAC|TACGTCGGAC|ACAAGGGCAA|GTTCGGGCAC 60|
|GAATTCTTGG|AGTTCGAGTT|CCGGCCGGAT|GGCAAGCTGC|GGTACGCCAA|CAACTCCAAC 120|
|TACAAGAACG|ACACCATGAT|CCGCAAGGAG|GCCTTCGTCC|ACCAGTCCGT|GATGGAAGAA 180|
|CTGAAGCGAA|TCATCATCGA|CTCGGAGATC|ATGCAGGAGG|ACGATCTGCC|CTGGCCGCCA 240|
|CCAGATCGCG|TGGGTCGACA|GGAACTGGAG|ATCGTCATCG|GAGACGAGCA|CATCTCGTTC 300|
|ACCACCTCGA|AAACGGGATC|ATTGGTGGAC|GTGAACCGGT|CAAAAGATCC|CGAGGGCCTG 360|
|CGATGCTTTT|ACTACCTGGT|GCAGGATCTC|AAGTGCCTGG|TCTTCTCACT|CATCGGCCTG 420|

CATTTCAAGA TCAAGCCCAT ATAA 444

(2) INFORMATION FOR SEQ ID NO:8:

(i) SEQUENCE CHARACTERISTICS:
(A) LENGTH: 147 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:8:

Met Ser Thr Glu Asp Phe Tyr Leu Arg Tyr Tyr Val Gly His Lys Gly
1               5                   10                  15

Lys Phe Gly His Glu Phe Leu Glu Phe Glu Phe Arg Pro Asp Gly Lys
            20                  25                  30

Leu Arg Tyr Ala Asn Asn Ser Asn Tyr Lys Asn Asp Thr Met Ile Arg
        35                  40                  45

Lys Glu Ala Phe Val His Gln Ser Val Met Glu Glu Leu Lys Arg Ile
    50                  55                  60

Ile Ile Asp Ser Glu Ile Met Gln Glu Asp Asp Leu Pro Trp Pro Pro
65                  70                  75                  80

Pro Asp Arg Val Gly Arg Gln Glu Leu Glu Ile Val Ile Gly Asp Glu
                85                  90                  95

His Ile Ser Phe Thr Thr Ser Lys Thr Gly Ser Leu Val Asp Val Asn
            100                 105                 110

Arg Ser Lys Asp Pro Glu Gly Leu Arg Cys Phe Tyr Tyr Leu Val Gln
        115                 120                 125

Asp Leu Lys Cys Leu Val Phe Ser Leu Ile Gly Leu His Phe Lys Ile
    130                 135                 140

Lys Pro Ile
145

(2) INFORMATION FOR SEQ ID NO:9:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

AGTGTCGACC TATCTGGGGT TGTTGAGGAG GAT 33

(2) INFORMATION FOR SEQ ID NO:10:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

CGGGATCCGT GCTGCTGCTA TGTCCAGAAT GGGCAAACCC AT 42

(2) INFORMATION FOR SEQ ID NO:11:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

GGGGTCGACT TAAATTGGTT TAATCTTGAA GTG    33

( 2 ) INFORMATION FOR SEQ ID NO:12:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:12:

GGAATTCGCT GCTGCTATGG CTGTGGCTAG CGATTT    36

( 2 ) INFORMATION FOR SEQ ID NO:13:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:13:

GAAAUCGCUA GCCACAGCCA AAGCAGANNN NUCUGAGNAG UCUUUUGUAC C    51

( 2 ) INFORMATION FOR SEQ ID NO:14:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: YES ( x i ) SEQUENCE DESCRIPTION: SEQ ID NO:14:

CATTTTTGTA CCCGGGAAGC CGCCGAAAA ACG    33

CONSERVIN NUCLEIC ACID MOLECULES AND COMPOSITIONS

1. BACKGROUND OF THE INVENTION

The transforming growth factor-beta (TGFβ) family of structurally related paracrine polypeptides are found ubiquitously in vertebrates, and are prototypic of a large family of metazoan growth, differentiation, and morphogenesis factors (see, for review, Massaque et al. (1990) *Ann Rev Cell Biol* 6:597–641; Massaque et al. (1994) *Trends Cell Biol.* 4:172–178; Kingsley (1994) *Gene Dev.* 8:133–146; and Sporn et al. (1992) *J Cell Biol* 119:1017–1021). As described in Kingsley, supra, the TGFβ superfamily has at least 25 members, and can be grouped into distinct subfamilies with highly related sequences. The most obvious subfamilies include the following: the TGFβ sub-family, which comprises at least four genes that are much more similar to TGFβ-1 than to other members of the TGFβ superfamily; the activin sub-family, comprising homo- or heterodimers or two subunits, inhibinβ-A and inhibinβ-B; the decapentaplegic (DPP) subfamily, which includes the mammalian factors BMP2 and BMP4, which can induce the formation of ectopic bone and cartilage when implanted under the skin or into muscles; and the 60A sub-family, which includes a number of mammalian homologs, with osteoinductive activity, including BMP5-8. Other members of the TGFβ superfamily include the gross differentiation factor 1 (GDF-1), GDF-3/VGR-2, dorsalin, nodal, mullerian-inhibiting substance (MIS), and glial-derived neurotrophic growth factor (GDNF). The DPP and 60A subfamilies are related more closely to one another than to other members of the TGFβ superfamily, and have often been grouped together as part of a larger collection of molecules called DVR (dpp and vg1 related).

Signals transduced by the TGFβ superfamily of molecules play salient roles in numerous diverse biologic processes, including inflammation and host defense, in addition to development, tissue repair, and tumorigenesis (Wahl. 1994. *J. Exp. Med.* 180:1587). Members of the family are initially synthesized as larger precursor molecules with an amino-terminal signal sequence and a pro-domain of varying size (Kingsley, D. M. (1994) *Genes Dev.* 8:133–146). The precursor is then cleaved to release a mature carboxy-terminal segment of 110–140 amino acids. The active signaling moiety is comprised of hetero- or homodimers of the carboxy-terminal segment (Massague, J. (1990) *Annu. Rev. Cell Biol.* 6:597–641). The active form of the molecule then interacts with its receptor, which for this family of molecules is composed of two distantly related transmembrane serine/threonine kinases called type I and type II receptors (Massague, J. et al. (1992) *Cell* 69:1067–1070; Miyazono, K. A. et al. *EMBO J.* 10:1091–1101). TGFβ binds directly to the type II receptor, which then recruits the type I receptor and modifies it by phosphorylation. The type I receptor then transduces the signal to downstream components, which are as yet unidentified (Wrana et al, (1994) *Nature* 370:341–347).

Several members of the TGFβ superfamily have been identified which play roles during mammalian development. For example, dorsalin is expressed preferentially in the dorsal side of the developing chick neural tube (Basler et al. (1993)*Cell* 73:687–702). It promotes the outgrowth of neural crest cells and inhibits the formation of motor neuron cells in vitro, suggesting that it plays an important role in neural patterning along the dorsoventral axis. Certain of the bone morphogenetic proteins (BMPS) can induce the formation of ectopic bone and cartilage when implanted under the skin or into muscles (Wozney, J. M. et al. (1988) *Science* 242:1528–1534). Members of the activin subfamily have been found to be important in mesoderm induction during Xenopus development (Green and Smith (1990) *Nature* 47:391–394; Thomsen et al. (1990) *Cell* 63:485–493) and inhibins were initially described as gonadal inhibitors of follicle-stimulating hormone from pituitary cells. In addition, antagonists of this signaling pathway can be used to convert embryonic tissue into ectoderm, the default pathway of development in the absence of TGFβ-mediated signals. BMP-4 and activin have been found to be potent inhibitors of neuralization (Wilson, P. A. and Hemmati-Brivanlou, A (1995) *Nature* 376:331–333).

Further evidence for the importance of a TGFβ family member in early mammalian development comes from a retroviral insertion in the mouse nodal gene. This insertion leads to a failure to form the primitive streak in early embryogenesis, a lack of axial mesoderm tissue, and an overproduction of ectoderm and extraembryonic ectoderm (Conlon et al. (1991) *Development* 111:969–981; Iannaccone et al (1992) *Dev. Dynamics* 194:198–208). The predicted nodal gene product is consistent with previous studies showing that nodal is related to activins and BMPs (Zhou et al. (1993) *Nature* 361:543–547). A role for TGFβ family members in the development of sex organs has also been described; Mullerian inhibitory substance functions during mammalian male sexual development to cause regression of the embryonic duct system that develops into oviducts and uterus (Lee and Donahoe (1993) *Endocrinol. Rev.* 14:152–164).

Members of this family of signaling molecules also continue to function postdevelopment. TGFβ has a variety of pleiotropic effects on the immune system; it is capable of both stimulating inflammation, and immunosuppression. The apparent contradictory role of TGFβ in the immune system may, in part, be accounted for by differential effects of TGFβ on resting and activated cells (Wahl, supra.). Animals which cannot produce TGFβ1 (homozygous for null mutations in the TGFβ1 gene) have been found to survive until birth with no apparent morphological abnormalities (Shull et al. (1992) *Nature* 359:693–699; Kulkami et al. (1993) *Proc. Natl. Acad. Sci.* 90:770–774). The animals do die around weaning age, however, owing to massive immune infiltration in many different organs, consistent with the inhibitory effects of TGFβ on lymphocyte growth (Tada et al. (1991) *J. Immunol* 146:1077–1082). The adminsitration of TGFβ has been found to ameliorate experimental autoimmune encephalomyelitis and experimentally induced arthritis, thus demonstrating that modulation of TGFβ is a viable treatment for certain human autoimmune diseases (Border and Nobel, 1995 *Nature Medicine* 1:1000).

TGFβ can also promote neovascularization and the proliferation of connective tissue cells. Because of these activities, it plays a key role in wound healing (Kovacs, E. J. (1991) *Immunol Today* 12:17–23). Under normal conditions, TGFβ maintains cell numbers in the extracellular matrix by directly inhibiting cell proliferation and controlling the activity of platelet derived growth factor (Border and Nobel. supra.). Misexpression of TGFβ has been implicated in several disease processes, such as impaired wound healing in the elderly or diabetics. On the other hand, overproduction of TGFβ leads to the accumulation of pathological amounts of extracellular matrix, and may mediate fibrotic disorders affecting kidney, liver, lung, bone marrow, heart and skin (Border and Noble. 1994. *New Engl. J. Med.*

331:1286). Therefore, modulation of TGFβ may be useful in the treatment of disorders involving inappropriate healing and fibrosis.

Another proliferative disorder in which TGFβ has been implicated is the development of the atherosclerotic plaque. The advanced lesions of atherosclerosis result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures. Lipoprotein has been shown to inhibit TGFβ activation (Kojima et al. *J. Cell Biol.* 113:1439). The earliest lesion in atherosclerosis is the fatty streak, comprising lipid, macrophages, and T cells, which leads to smooth muscle cell proliferation and the development of more severe lesions (Ross. 1993 *Nature* 362:801). Transgenic mice which overexpress lipoprotein have been shown to have decreased levels of active TGFβ in serum and in the aortic wall (Grainger et al. 1995. *Nature Med.* 1:1067). In addition, treatment with tamoxifen, a known stimulator of TGFβ, can suppress the development of the fatty streak lesion in mice (Grainger et al. supra). Finally, treatment with anti-TGFβ has blocked intimal hyperplasia and restenosis in a rat model (Nikol et al. 1992. *J. Clin. Invest.* 90:1582).

Certain members of the TGFβ family have potent antiproliferative effects. In certain cancer cells conversion to a tumorigenic phenotype has been shown to be accompanied by reduced response to the growth-inhibitory effects of TGFβ (Manning et al. 1991. Oncogene 6:1471). Moreover, abnormalities in TGFβ receptors have been identified in several human maliganacies (Markowitz et al. 1995. Science. 268:1336). Recently, a role for members of the TGF-β superfamily has been postulated in tumor suppression (Hahn et al. 1996. Science 271:350). A gene, referred to as DPC4, has been found to be homozygously deleted in approximately 30% of pancreatic carcinomas tested. DPC4 was found to be homologous to the *Drosophila melanogaster* MAD gene and the sma-2, sma-3, and sma-4 genes of *C. elegans* (Hahn et al. supra), members of the DPP signaling subfamily of TGFβ molecules. Xenopus homologues of MAD have recently been cloned and have been shown to be important in the induction of mesoderm (Graff et al. 1996. *Cell* 85:479). MADs function downstream of TGFβ receptors and may function in the nucleus (Hoodless et al. 1996. *Cell* 85:489). Applicant has found MAD to be homologous to the fchd534 gene.

2. SUMMARY OF THE INVENTION

The present invention is based on the discovery of novel molecules, referred to herein as "conservin" nucleic acid and polypeptide molecules. Exemplary conservin molecules referred to hereinafter as human conservin1 and conservin2 are contained in *E. coli* plasmids p12b1 and p15c2, which were deposited with the American Type Culture Collection (ATCC) on May 8, 1996 and have been assigned ATCC designation numbers 98049 and 98048, respectively. The human conservin genes, which are approximately 444 for conservin1 and 438 for conservin2 base pairs in length, are expressed in numerous tissues, including spleen, thymus, prostate, testes, ovary, small intestine, colon, and peripheral blood cells, among others. The human conservin genes encode polypeptides of approximately 17 kD. The full length conservin1 polypeptide comprises 148 amino acids and the conservin2 polypeptide comprises 146 amino acids.

In one aspect, the invention features isolated vertebrate conservin nucleic acid molecules. The disclosed molecules can be non-coding, (e.g. probe, antisense or ribozyme molecules) or can encode a functional conservin polypeptide (e.g. a polypeptide which specifically modulates, e.g., by acting as either an agonist or antagonist, at least one bioactivity of the human conservin polypeptide). In one embodiment, the nucleic acid molecules hybridize to the conservin gene contained in *E. coli* plasmids p12b1 and p15c2 or to the complement of the conservin gene contained in *E. coli* plasmids p12b1 and p15c2. In another embodiment, the nucleic acids of the present invention can hybridize to a vertebrate conservin gene or to the complement of a vertebrate conservin gene. In a further embodiment, the claimed nucleic acid hybridizes with the coding sequence designated in at least one of SEQ ID NOS:1, 2, 4 or 5 or to the complement to the coding sequence designated in at least one of SEQ ID NOS:1, 2, 4 or 5. In a preferred embodiment, the hybridization is conducted under mildly stringent or stringent conditions.

In further embodiments, the nucleic acid molecule is a conservin nucleic acid that is at least 70%, preferably 80%, more preferably 85%, and even more preferably at least 95% homologous in sequence to the nucleic acids shown as SEQ ID NOS:1, 2, 4 or 5 or to the complement of the nucleic acids shown as SEQ ID NOS:1, 2, 4 or 5. In another embodiment, the conservin nucleic acid molecule encodes a polypeptide that is at least 92.5% and more preferably at least 94% similar in sequence to the polypeptide shown in SEQ ID NOS:3 or 6. In a further embodiment, the nucleic acid molecule is a conservin nucleic acid that is at least 70%, preferably 80%, more preferably 85% and even more preferably at least 90% or 95% similar in sequence to the conservin gene contained in *E. coli* plasmids p12b1 and p15c2 or to the complement of the conservin gene contained in *E. coli* plasmids p12b1 and p15c2

The invention also provides probes and primers comprising substantially purified oligonucleotides, which correspond to a region of nucleotide sequence which hybridizes to at least 6 consecutive nucleotides of the sequences set forth as SEQ ID NOS:1 or 3 or complements of the sequences set forth as SEQ ID NOS:1, 2, 4 or 5, or naturally occurring mutants thereof. In preferred embodiments, the probe/primer further includes a label group attached thereto, which is capable of being detected.

For expression, the subject conservin nucleic acids can include a transcriptional regulatory sequence, e.g. at least one of a transcriptional promoter (e.g., for constitutive expression or inducible expression) or transcriptional enhancer sequence, which regulatory sequence is operably linked to the conservin gene sequence. Such regulatory sequences in conjunction with a conservin nucleic acid molecules can be useful vectors for gene expression. This invention also describes host cells transfected with said expression vector whether prokaryotic or eukaryotic and in vitro (e.g. cell culture) and in vivo (e.g. transgenic) methods for producing conservin proteins by employing said expression vectors.

In another aspect, the invention features isolated conservin polypeptides, preferably substantially pure preparations e.g. of plasma purified or recombinantly produced conservin polypeptides. In preferred embodiments, the polypeptide is able to bind to a FCHD534 polypeptide and/or to modulate an intracellular signaling pathway involving TGFβ. In other embodiments, the subject polypeptides are capable of modulating one or more of the growth, differention, and/or proliferation of a cell. In preferred embodiments, the subject conservin polypeptides can suppress the development and/or progression of cardiovascular disease. In addition, conservin polypeptides which specifically antagonize the activity of a native conservin polypeptide, such as may be provided by truncation mutants or other dominant negative mutants, are also specifically provided for.

In one embodiment, the polypeptide is identical to or similar to a conservin protein represented in one of SEQ ID NOS:3 or 6. Related members of the vertebrate and particularly the mammalian conservin family are also within the scope of the invention. Preferably, a conservin polypeptide has an amino acid sequence at least 92.5% homologous, preferably at least 94%, more preferably at least 95%, and even more preferably at least 98–99% homologous to the polypeptide represented by one of SEQ ID NOS:3 or 6. In a preferred embodiment, the conservin polypeptide is encoded by a nucleic acid which hybridizes with a nucleic acid sequence represented in one of SEQ ID NOS:1, 2, 4, or 5 or with the gene or gene fragment contained in clones p12b1 (ATCC Accession No. 98049) and p15c2 (ATCC Accession No. 98048). The subject conservin proteins also include modified protein, which are resistant to post-translation modification, as for example, due to mutations which alter modification sites (such as tyrosine, threonine, serine or aspargine residues), or which prevent glycosylation of the protein, or which prevent interaction of the protein with intracellular proteins involved in signal transduction.

The conservin polypeptide can comprise a full length protein, such as represented in one of SEQ ID NOS:3 or 6, or it can comprise a fragment corresponding to one or more particular motifs/domains, or to arbitrary sizes, e.g., at least 5, 10, 25, 50, 100, 150 or 200 amino acids in length. In preferred embodiments, the conservin polypeptide includes a sufficient portion of an interacting domain (e.g., a 534 protein binding domain). A particularly preferred conservin polypeptide has a molecular weight of about 17 kd.

Another aspect of the invention features chimeric molecules (e.g. fusion proteins) comprised of a conservin protein. For instance, the conservin protein can be provided as a recombinant fusion protein which includes a second polypeptide portion, e.g., a second polypeptide having an amino acid sequence unrelated (heterologous) to the conservin polypeptide, (e.g. the second polypeptide portion is glutathione-S-transferase, an enzymatic activity such as alkaline phosphatase or an epitope tag).

Yet another aspect of the present invention concerns an immunogen comprising a conservin polypeptide in an immunogenic preparation, the immunogen being capable of eliciting an immune response specific for a conservin polypeptide; e.g. a humoral response, an antibody response and/or cellular response. In preferred embodiments, the immunogen comprises an antigenic determinant, e.g. a unique determinant, from the protein represented by on of SEQ ID NOS:3 or 6.

A still further aspect of the present invention features antibodies and antibody preparations specifically reactive with an epitope of the conservin protein. In preferred embodiments the antibody specifically binds to an epitope represented in SEQ ID NOS:3 or 6.

The invention also features transgenic non-human animals which include (and preferably express) a heterologous form of a conservin gene described herein, or which mis-express an endogenous conservin gene (e.g., an animal in which expression of one or more of the subject conservin proteins is disrupted). Such a transgenic animal can serve as an animal model for studying cellular and tissue disorders comprising mutated or mis-expressed conservin alleles or for use in drug screening. Alternatively, such a transgenic animal can be useful for expressing recombinant conservin polypeptides.

In yet another aspect, the invention provides assays, e.g., for screening test compounds to identify inhibitors, or alternatively, potentiators, of an interaction between a conservin protein and, for example, a virus, an extracellular ligand of the conservin protein, or an intracellular protein which binds to the conservin protein (eg., a substrate of the conservin phosphatase activity). An exemplary method includes the steps of (i) combining a conservin polypeptide or bioactive fragments thereof, a conservin target molecule (such as a conservin ligand or a conservin substrate), and a test compound, e.g., under conditions wherein, but for the test compound, the conservin protein and target molecule are able to interact; and (ii) detecting the formation of a complex which includes the conservin protein and the target polypeptide either by directly quantitating the complex, by measuring inductive effects of the conservin protein, or, in the instance of a substrate, measuring the conversion to product. A statistically significant change, such as a decrease, in the interaction of the conservin and target molecule in the presence of a test compound (relative to what is detected in the absence of the test compound) is indicative of a modulation (e.g., inhibition or potentiation of the interaction between the conservin protein and the target molecule).

Yet another aspect of the present invention concerns a method for modulating the growth, differentiation, and/or survival of a cell by modulating conservin bioactivity, (e.g., by potentiating or disrupting certain protein-protein interactions). In general, whether carried out in vivo, in vitro, or in situ, the method comprises treating the cell with an effective amount of a conservin therapeutic so as to alter, relative to the cell in the absence of treatment, at least one of (i) rate of growth, (ii) differentiation, or (iii) survival of the cell. Accordingly, the method can be carried out with conservin therapeutics such as peptide and peptidomimetics or other molecules identified in the above-referenced drug screens which agonize or antagonize the effects of signaling from a conservin protein or ligand binding of a conservin protein. Other conservin therapeutics include antisense constructs for inhibiting expression of conservin proteins, and dominant negative mutants of conservin proteins which competitively inhibit ligand interactions upstream and signal transduction downstream of the wild-type conservin protein.

A further aspect of the present invention provides a method of determining if a subject is at risk for a disorder characterized by unwanted cell proliferation or aberrant control of differentiation or apoptosis. The method includes detecting, in a tissue of the subject, the presence or absence of a genetic lesion characterized by at least one of (i) a mutation of a gene encoding a conservin protein, e.g. represented in one of SEQ ID NOS:1, 2, 4, or 5 or a homolog thereof; or (ii) the mis-expression of a conservin gene. In preferred embodiments, detecting the genetic lesion includes ascertaining the existence of at least one of: a deletion of one or more nucleotides from a conservin gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble conservin protein.

For example, detecting the genetic lesion can include (i) providing a probe/primer comprised of an oligonucleotide which hybridizes to a sense or antisense sequence of a conservin gene or naturally occurring mutants thereof, or 5' or 3' flanking sequences naturally associated with the conservin gene; (ii) contacting the probe/primer to an appropriate nucleic acid containing sample; and (iii) detecting, by hybridization of the probe/primer to the nucleic acid, the presence or absence of the genetic lesion; e.g. wherein detecting the lesion comprises utilizing the probe/primer to determine the nucleotide sequence of the conservin gene and, optionally, of the flankininstance, the primer can. For instance, the primer can be employed in a polymerase chain reaction (PCR) or in a ligation chain reaction (LCR). In alternate embodiments, the level of a conservin protein is detected in an immunoassay using an antibody which is specifically immunoreactive with the conservin protein.

Other features and advantages of the invention will be apparent from the following detailed description and claims.

3. BRIEF DESCRIPTION OF THE FIGURES

FIG. 1 shows a DNA sequence of the human conservin1 gene including 5' and 3' noncoding sequences, as well as the deduced amino acid sequence of the conservin1 protein (SEQ ID NOS:1 and 3).

FIG. 2 shows a DNA sequence of the human conservin2 gene including 5' and 3' noncoding sequences, as well as the deduced amino acid sequence of the conservin2 protein (SEQ ID NOS:4 and 6).

FIG. 3 shows a comparison of the gene sequences of conservin1 (SEQ ID NO:1) and conservin2 (SEQ ID NO:4) with the *Drosophila mago* nashi gene sequence (SEQ ID NO:7).

FIG. 4 shows a comparison of the amino acid sequence of conservin1 (SEQ ID NO:3) and conservin2 (SEQ ID NO:6) with the *Drosophila mago* nashi amino acid sequence (SEQ ID NO:8).

4. DESCRIPTION OF THE INVENTION

4.1. General

The present invention is based on the discovery of a family of novel genes, referred to herein as "conservins", which function in biochemical pathways involving members of the TGFβ-superfamily. These novel molecules play a role in determining tissue fate and maintenance, cell proliferation, and tumorigenesis.

The conservin genes or gene products provided by the present invention are exemplified by conservin1 and conservin2. The mRNA transcripts and deduced amino acid sequences of conservin1 and conservin2 are shown in SEQ ID NOS:2, 3, 5, and 6, respectively. A comparison of the coding regions of the conservin1 and conservin2 genes are 85.2% homologous and that the amino acid sequences of the conservin1 and conservin2 proteins are 98% homologous.

From their apparent molecular weights, the family of conservin proteins are approximately 17 kD. The expression pattern of conservin, as determined by northern blot analyses, suggests a broad tissue distribution. Expression has been detected in, for example, spleen, thymus, prostate, testes, ovary, small intestin, colon, and peripheral blood cells, among others.

The conservin genes are similar in sequence to the *mago* nashi gene of *Drosophila melanogaster*. (See FIGS. 3 and 4). A comparison of the nucleic acid sequences reveals that the conservin genes are approximately 70% similar to the *Drosophila mago* nashi gene. Further, a comparison of the amino acid sequences reveals that the conservin1 amino acid sequence is approximately 91% similar to the *mago* nashi amino acid sequence and that the conservin2 amino acid sequence is approximately 92% similar to the *mago* nashi amino acid sequence. Studies have shown that the *mago* nashi locus encodes an essential product required for germ plasm assembly in Drosophila (Newmark, P. A. and R. E. Boswell (1994) *Development* 120: 1303–1313; Boswell, R. E. et al., (1991) *Development* 113:373–384).

The cDNAs corresponding to conservin gene transcripts were initially cloned from human breast tissue based on the ability of their encoded proteins to bind to the FCHD534 gene product in an assay that detects protein/protein interactions, placing the conservin gene products in the same biochemical pathway as FCHD534. The human FCHD534 protein was previously identified based on its differential expression in an experimental paradigm of cardiovascular disease. The fchd534 gene was deposited with the Agricultural Research Service Culture Collection (NRRL), Peoria, Ill., on Jun. 6, 1995 and assigned accession number B-21458. FCHD534 was found to have homology to the C-terminus of Drosophila MAD and its homologue, DCP4. FCHD534 was also found to map to the same region of chromosome 18 as DCP4, a region of that chromosome known to be deleted in certain cancers (Hahn et al. supra).

MAD is an intracellular signaling molecule which functions in the TGFβ signaling pathway (Serra and Moses. 1996. *Nature Medicine.* 2:390). Because of its sequence similarity to MAD, fchd534 can also be placed in this pathway. Furthermore, by virtue of their ability to bind to and/or interact with the FCHD534 gene product, the conservin proteins may also be placed in this pathway. Members of the TGFβ superfamily include: the TGFβ sub-family; the activin sub-family; the DVR sub-family; gross differentiation factor 1 (GDF-1); GDF-3/VGR-2; dorsalin; nodal; mullerian-inhibiting substance (MIS); or glial-derived neurotrophic growth factor (GDNF). In preferred embodiments, the conservin proteins of the present invention are capable of modulating signals by members of the DPP subfamily of TGFβ molecules.

In addition to the conservin gene transcripts, two other genes were simultaneously detected based on the ability of their encoded proteins to bind to the FCHD534 gene product in the two hybrid assay. One of the genes, (BLAST accession number X74796), has been previously described as being a member of the mammalian P1 family of nuclear proteins that are related to the yeast Mcm replication proteins (Hu, B. et al., (1993) *Nucl. Acids Res.* 21:5289–5293). The other gene, SUPT6H (BLAST accession number U46691) is though to encode a 1603 amino acid protein that is thought to regulate transcription through establishment or maintenance of chromatin structure (Chiang, P.-W. et al., (1996) *Genomics* 34:328–333).

Accordingly, certain aspects of the present invention relate to nucleic acid molecules encoding mammalian conservin proteins, the conservin proteins, antibodies immunoreactive with conservin proteins, and preparations of such compositions. In addition, drug discovery assays are provided for identifying agents which can modulate the biological function of conservin proteins, such as by altering the interaction of mammalian conservin molecules with either downstream or upstream elements in the FCHD534 signal transduction pathway. Such agents can be useful therapeutically, for example, to alter the growth and/or differentiation of a cell. Moreover, the present invention provides diagnostic and therapeutic assays and reagents for detecting and treating disorders involving, for example, aberrant expression (or loss thereof) of mammalian conservin genes. Other aspects of the invention are described below or will be apparent to those skilled in the art in light of the present disclosure.

4.2 Definitions

For convenience, the meaning of certain terms and phrases employed in the specification, examples, and appended claims are provided below.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject mammalian conservin polypeptides with a second amino acid sequence defining a domain (e.g. polypeptide portion) foreign to and not substantially homologous with any domain of one of the mammalian conservin proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-conservin-Y, wherein conservin represents a portion of the protein which is derived from one of the mammalian conservin proteins, and X and Y are independently absent or represent amino acid sequences which are not related to one of the mammalian conservin sequences in an organism, including naturally occurring mutants.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a mammalian conservin polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

As used herein, the term "gene" or "recombinant gene" refers to a nucleic acid molecule comprising an open reading frame encoding one of the mammalian conservin polypeptides of the present invention, including both exon and (optionally) intron sequences. A "recombinant gene" refers to nucleic acid encoding a mammalian conservin polypeptide and comprising mammalian conservin-encoding exon sequences, though it may optionally include intron sequences which are either derived from a chromosomal mammalian conservin gene or from an unrelated chromosomal gene. Exemplary recombinant genes encoding the subject mammalian conservin polypeptides are represented in the appended Sequence Listing. The term "intron" refers to a DNA sequence present in a given mammalian conservin gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the mammalian conservin sequences of the present invention.

The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject mammalian conservin polypeptides preferably includes no more than 10 kilobases (kb) of nucleic acid sequence which naturally immediately flanks the mammalian conservin gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation, i.e., stimulation, and downregulation, i.e. suppression, of a response.

The "non-human animals" of the invention include mammalians such as rodents, non-human primates, sheep, dog, cow, chickens, amphibians, reptiles, etc. preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue-specific chimeric animal" indicates that one of the recombinant mammalian conservin genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The terms "protein", "polypeptide" and "peptide" are used interchangably herein when referring to a gene product.

The term "recombinant protein" refers to a polypeptide of the present invention which is produced by recombinant DNA techniques, wherein generally, DNA encoding a mammalian conservin polypeptide is inserted into a suitable expression vector which is in turn used to transform a host cell to produce the heterologous protein. Moreover, the phrase "derived from", with respect to a recombinant conservin gene, is meant to include within the meaning of "recombinant protein" those proteins having an amino acid sequence of a native conservin protein, or an amino acid sequence similar thereto which is generated by mutations including substitutions and deletions (including truncation) of a naturally occurring form of the protein.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably mammalian, conservin gene, such as a conservin sequence designated in one of SEQ ID NOS:1, 2, 4 or 5, or a sequence complementary thereto, or naturally occurring mutants thereof, such that it shows more than 10 times more hybridization, preferably more than 100 times more hybridization, and even more preferably more than 100 times more hybridization than it does to to a cellular nucleic acid (e.g., mRNA or genomic DNA) encoding a protein other than a vertebrate, preferably mammalian, conservin protein as defined herein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of hepatic or pancreatic origin, neuronal cells, or immune cells. The term also covers so-called "leaky" promoters, which regulate expression of a selected DNA primarily in one tissue, but cause expression in other tissues as well.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant mammalian conservin genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of conservin proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian conservin polypeptide or, in the case of anti-sense expression from the transferred gene, the expression of a naturally-occurring form of the conservin protein is disrupted.

As used herein, the term "transgene" means a nucleic acid sequence (encoding, e.g., one of the mammalian conservin polypeptides, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the mammalian conservin proteins, e.g. either agonistic or antagonistic forms. However, transgenic animals in which the recombinant conservin gene is silent are also contemplated, as for example, the FLP or CRE recombinase dependent constructs described below. Moreover, "transgenic animal" also includes those recombinant animals in which gene disruption of one or more conservin genes is caused by human intervention, including both recombination and antisense techniques.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3 Nucleic Acids of the Present Invention

As described below, one aspect of the invention pertains to isolated nucleic acids comprising nucleotide sequences encoding conservin1 or conservin2 conservin polypeptides, and/or equivalents of such nucleic acids. The term equivalent is understood to include nucleotide sequences encoding functionally equivalent conservin polypeptides or functionally equivalent peptides having an activity of a vertebrate conservin protein such as described herein. Equivalent nucleotide sequences will include sequences that differ by one or more nucleotide substitutions, additions or deletions, such as allelic variants; and will, therefore, include sequences that differ from the nucleotide sequence of the conservin gene shown in any of SEQ ID NOS:1, 2, 4 or 5 due to the degeneracy of the genetic code.

Preferred nucleic acids are vertebrate conservin nucleic acids. Particularly preferred vertebrate conservin nucleic acids are mammalian. Regardless of species, particularly preferred conservin nucleic acids encode polypeptides that are at least 90% similar to an amino acid sequence of a vertebrate conservin. preferred nucleic acids encode a conservin polypeptide comprising an amino acid sequence at least 92.5% homologous and more preferably 94% homologous with an amino acid sequence of a vertebrate conservin, e.g., such as a sequence shown in one of SEQ ID NOS:3 or 6. Nucleic acids which encode polypeptides at least about 95%, and even more preferably at least about 98–99% similarity with an amino acid sequence represented in one of SEQ ID NOS:3 or 6 are also within the scope of the invention. In a particularly preferred embodiment, the nucleic acid of the present invention encodes an amino acid conservin sequence shown in one of SEQ ID NOS:3 or 6. In one embodiment, the nucleic acid is a cDNA encoding a peptide having at least one boactivity of the subject conservin polypeptide. preferably, the nucleic acid includes all or a portion of the nucleotide sequence corresponding to the coding region of SEQ ID NOS:1 or 4.

Still other preferred nucleic acids of the present invention encode a conservin polypeptide which includes a polypeptide sequence corresponding to all or a portion of amino acid residues of SEQ ID NO:3 or of SEQ ID NO:6, e.g., at least 2, 5, 10, 25, 50, 100, 150 or 200 amino acid residues of that region. For example, preferred nucleic acid molecules for use as probes/primer or antisense molecules (i.e. noncoding nucleic acid molecules) can comprise at least about 6, 12, 20, 30, 50, 100, 125, 150 or 200 base pairs in length, whereas coding nucleic acid molecules can comprise about 200, 250, 300, 350, 400, 410, 420, 430, 435 or 440 base pairs.

Another aspect of the invention provides a nucleic acid which hybridizes under stringent conditions to a nucleic acid represented by one of SEQ ID NOS:1, 2, 4, or 5. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current protocols in Molecular Biology, John Wiley & Sons, New York (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a conservin nucleic acid of the present invention will bind to one of SEQ ID NOS:1, 2, 4 or 5 under moderately stringent conditions, for example at about 2.0× SSC and about 40° C. In a particularly preferred embodiment, a conservin nucleic acid of the present invention will bind to one of SEQ ID NOS:1, 2, 4 or 5 under high stringency conditions, but will not bind to the nucleic acid shown in SEQ ID NO:7.

Preferred nucleic acids have a sequence at least 75% homologous and more preferably 80% and even more preferably at least 85% homologous with a nucleotide sequence of a mammalian conservin, e.g., such as a sequence shown in one of SEQ ID NOS:1 and 3. Nucleic acids at least 90%, more preferably 95%, and most preferably at least about 98–99% homologous with a nucleic sequence represented in one of SEQ ID NOS:1, 2, 4, or 5 are of course also within the scope of the invention. In preferred embodiments, the nucleic acid is a mammalian conservin gene and in particularly preferred embodiments, includes all or a portion of the nucleotide sequence corresponding to the coding region of one of SEQ ID NOS: 1, 2, 4, or 5.

Nucleic acids having a sequence that differs from the nucleotide sequences shown in one of SEQ ID NOS:1, 2, 4, or 5 due to degeneracy in the genetic code are also within the scope of the invention. Such nucleic acids encode functionally equivalent peptides (i.e., a peptide having a biological activity of a mammalian conservin polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a mammalian conservin polypeptide. However, it is expected that DNA sequence polymorphisms that do lead to changes in the amino acid sequences of the subject conservin polypeptides will exist among mammalians. One skilled in the art will appreciate that these variations in one or more nucleotides (e.g., up to about 3–5% of the nucleotides) of the nucleic acids encoding polypeptides having an activity of a mammalian conservin polypeptide may exist among individuals of a given species due to natural allelic variation.

As indicated by the examples set out below, conservin protein-encoding nucleic acids can be obtained from mRNA present in any of a number of eukaryotic cells. It should also be possible to obtain nucleic acids encoding mammalian conservin polypeptides of the present invention from genomic DNA from both adults and embryos. For example, a gene encoding a conservin protein can be cloned from either a cDNA or a genomic library in accordance with protocols described herein, as well as those generally known to persons skilled in the art. Examples of tissues and/or libraries suitable for isolation of the subject nucleic acids include breast, spleen, thymus, prostate, testes, ovary, small intestine, colon, and peripheral blood cells, among others. A cDNA encoding a conservin protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian conservin protein can also be cloned using established polymerase chain reaction techniques in accordance with the nucleotide sequence information provided by the invention. The nucleic acid of the invention can be DNA or RNA. A preferred nucleic acid is a cDNA represented by a sequence selected from the group consisting of SEQ ID NOS:1, 2, 4, or 5.

4.3.1. Vectors

This invention also provides expression vectors containing a nucleic acid encoding a conservin polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject mammalian conservin proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a subject conservin polypeptide, or alternatively, encoding a peptide which is an antagonistic form of the conservin protein. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject mammalian conservin proteins. Thus, another aspect of the invention features expression vectors for in vivo or in vitro transfection and expression of a mammalian conservin polypeptide in particular cell types so as to reconstitute the function of, or alternatively, abrogate the function of conservin-induced signaling in a tissue. This could be desirable, for example, when the naturally-occurring form of the protein is misexpressed; or to deliver a form of the protein which alters differentiation of tissue. Expression vectors may also be employed to inhibit neoplastic transformation.

In addition to viral transfer methods, such as those illustrated above, non-viral methods can also be employed to cause expression of a subject conservin polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject conservin polypeptide gene by the targeted cell. Exemplary targeting means of this type include liposomal derived systems, poly-lysine conjugates, and artificial viral envelopes.

4.3.2. Probes and Primers

Moreover, the nucleotide sequences determined from the cloning of conservin genes from mammalian organisms will further allow for the generation of probes and primers designed for use in identifying and/or cloning conservin homologs in other cell types, e.g. from other tissues, as well as conservin homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID NOS:1, 2, 4, or 5, or naturally occurring mutants thereof. For instance, primers based on the nucleic acid represented in SEQ ID NOS:1, 2, 4, or 5 can be used in PCR reactions to clone conservin homologs. preferred primers of the invention are set forth as SEQ ID NOS:9–12.

Likewise, probes based on the subject conservin sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme co-factors.

As discussed in more detail below, such probes can also be used as a part of a diagnostic test kit for identifying cells or tissue which misexpress a conservin protein, such as by measuring a level of a conservin-encoding nucleic acid in a sample of cells from a patient; e.g. detecting conservin mRNA levels or determining whether a genomic conservin gene has been mutated or deleted. Briefly, nucleotide probes can be generated from the subject conservin genes which facilitate histological screening of intact tissue and tissue samples for the presence (or absence) of conservin-encoding transcripts. Similar to the diagnostic uses of anti-conservin antibodies, the use of probes directed to conservin messages, or to genomic conservin sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described herein, the oligonucleotide probes can help facilitate the determination of the molecular basis for a developmental disorder which may involve some abnormality associated with expression (or lack thereof) of a conservin protein. For instance, variation in polypeptide synthesis can be differentiated from a mutation in a coding sequence.

4.3.3. Antisense, Ribozyme and Triplex techniques

One aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject conservin proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a mammalian conservin protein. Alternatively, the antisense construct is an oligonucleotide probe which is generated ex vivo and which, when introduced into the cell causes inhibition of expression by hybridizing with the mRNA and/or genomic sequences of a mammalian conservin gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the conservin nucleotide sequence of interest, are preferred.

Antisense approaches involve the design of oligonucleotides (either DNA or RNA) that are complementary to conservin mRNA. The antisense oligonucleotides will bind to the conservin mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. *Nature* 372:333). Therefore, oligonucleotides complementary to either the 5' or 3' untranslated, non-coding regions of a conservin gene could be used in an antisense approach to inhibit translation of endogenous conservin mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of conservin mRNA, antisense nucleic acids should be at least six nucleotides in length, and are preferably oligonucleotides ranging from 6 to about 50 nucleotides in length. In certain embodiments, the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. W088/09810, published Dec. 15, 1988) or the blood-brain barrier (see, e.g., PCT Publication No. W089/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc.

While antisense nucleotides complementary to the conservin coding region sequence could be used, those complementary to the transcribed untranslated region are most preferred. For example, an antisense oligonucleotide as set forth in SEQ ID NO:14 can be utilized in accordance with the invention.

The antisense molecules should be delivered to cells which express the conservin in vivo. A number of methods have been developed for delivering antisense DNA or RNA to cells; e.g., antisense molecules can be injected directly into the tissue site, or modified antisense molecules, designed to target the desired cells (ea., antisense linked to peptides or antibodies that specifically bind receptors or antigens expressed on the target cell surface) can be administered systematically.

However, it is often difficult to achieve intracellular concentrations of the antisense sufficient to suppress translation on endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous conservin transcripts and thereby prevent translation of the conservin mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave conservin mRNA transcripts can also be used to prevent translation of conservin mRNA and expression of conservin. (See, e.g., PCT International publication WO90/11364, published Oct. 4, 1990; Sarver et al., 1990, Science 247:1222–1225). While ribozymes that cleave mRNA at site specific recognition sequences can be used to destroy conservin mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are hundreds of potential hammerhead ribozyme cleavage sites within the nucleotide sequence of human conservin cDNA (FIG. 3). preferably the ribozyme is engineered so that the cleavage recognition site is located near the 5' end of the conservin mRNA; i.e., to increase efficiency and minimize the intracellular accumulation of non-functional mRNA transcripts.

For example, ribozymes having the sequence set forth in SEQ ID NO:13 can be utilized in accordance with the invention. The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in conservin.

As in the antisense approach, the ribozymes can be composed of modified oligonucleotides (e.g. for improved stability, targeting, etc.) and should be delivered to cells which express the conservin in vivo e.g., hypothalamus and/or the choroid plexus. A preferred method of delivery involves using a DNA construct "encoding" the robozyme under the control of a strong constitutive pol III or pol II promoter, so that transfected cells will produce sufficient quantities of the ribozyme to destroy endogenous conservin ages and inhibit translation. Because ribozymes unlike antisense molecules, are catalytic, a lower intracellular concentration is required for efficiency.

Endogenous conservin gene expression can also be reduced by inactivating or "knocking out" the conservin gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional conservin (or a completely unrelated DNA sequence) flanked by DNA homologous to the endogenous conservin gene (either the coding regions or regulatory regions of the conservin gene) can be used, with or without a selectable marker and/or a negative selectable marker, to transfect cells that express conservin in vivo. Insertion of the DNA construct, via targeted homologous recombination, results in inactivation of the conservin gene. Such approaches are particularly suited in the agricultural field where modifications to ES (embryonic stem) cells can be used to generate animal offspring with an inactive conservin (e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous conservin gene expression can be reduced by targeting deoxyribonucleotide sequences complementary to the regulatory region of the conservin gene (i.e., the conservin promoter and/or enhancers) to form triple helical structures that prevent transcription of the conservin gene in target cells in the body. (See generally, Helene, C. 1991, Anticancer Drug Des., 6(6):569–84; Helene, C., et al., 1992, Ann, New York Accad. Sci., 660:27–36; and Maher, L. J., 1992, Bioassays 14(12):807–15).

Likewise, the antisense constructs of the present invention, by antagonizing the normal biological activity of one of the conservin proteins, can be used in the manipulation of tissue, e.g. tissue differentiation, both in vivo and for ex vivo tissue cultures.

Furthermore, the anti-sense techniques (e.g. microinjection of antisense molecules, or transfection with plasmids whose transcripts are anti-sense with regard to a conservin mRNA or gene sequence) can be used to investigate role of conservin in developmental events, as well as the normal cellular function of conservin in adult tissue. Such techniques can be utilized in cell culture, but can also be used in the creation of transgenic animals, as detailed below.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding FCHD534 interactor proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.4. polypeptides of the Present Invention

The present invention also makes available isolated conservin polypeptides which are isolated from, or otherwise substantially free of other cellular proteins, especially other signal transduction factors and/or transcription factors which may normally be associated with the conservin polypeptide. The term "substantially free of other cellular proteins" (also referred to herein as "contaminating proteins") or "substantially pure or purified preparations" are defined as encompassing preparations of conservin polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified conservin preparations will lack any contaminating proteins from the same animal from which conservin is normally produced, as can be accomplished by recombinant expression of, for example, a human conservin protein in a non-human cell.

Full length proteins or fragments corresponding to one or more particular motifs and/or domains or to arbitrary sizes, for example, at least 5, 10, 25, 50, 75, 100, 125, 150 amino acids in length are within the scope of the present invention.

For example, isolated conservin polypeptides can include all or a portion of an amino acid sequences corresponding to a conservin polypeptide represented in one or more of SEQ ID NOS:3 or 6. Isolated peptidyl portions of conservin proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a conservin polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") conservin protein.

Another aspect of the present invention concerns recombinant forms of the conservin proteins. Recombinant polypeptides preferred by the present invention, in addition to native conservin proteins, are at least 92% homologous and more preferably 94% homologous and most preferably 95% homologous with an amino acid sequence represented by any of SEQ ID NOS:3 or 6. Polypeptides which are at least about 98–99% homologous with a sequence selected from the group consisting of SEQ ID NOS:3 or 6 are also within the scope of the invention. In a preferred embodiment, a conservin protein of the present invention is a mammalian conservin protein. In a particularly preferred embodiment a conservin protein comprises the coding sequence of one of SEQ ID NOS:3 or 6. In particularly preferred embodiments, a conservin protein has a conservin bioactivity.

In certain preferred embodiments, the invention features a purified or recombinant conservin polypeptide having a molecular weight of approximately 17 kD. It will be understood that certain post-translational modifications, e.g., phosphorylation and the like, can increase the apparent molecular weight of the conservin protein relative to the unmodified polypeptide chain.

The present invention further pertains to recombinant forms of one of the subject conservin polypeptides which are encoded by genes derived from a mammalian organism, and which have amino acid sequences evolutionarily related to the conservin proteins represented in SEQ ID NOS:3 and 6. Such recombinant conservin polypeptides preferably are capable of functioning in one of either role of an agonist or antagonist of at least one biological activity of a wild-type ("authentic") conservin protein of the appended sequence listing. The term "evolutionarily related to", with respect to amino acid sequences of mammalian conservin proteins, refers to both polypeptides having amino acid sequences which have arisen naturally, and also to mutational variants of mammalian conservin polypeptides which are derived, for example, by combinatorial mutagenesis. Such evolutionarily derived conservin polypeptides preferred by the present invention have a conservin bioactivity and are at least 92% homologous and more preferably 94% homologous and most preferably 98–99% homologous with the amino acid sequence selected from the group consisting of SEQ ID NOS:3 and 6. In a particularly preferred embodiment, a conservin protein comprises the amino acid coding sequence of one of SEQ ID NOS:3 or 6.

In general, polypeptides referred to herein as having an activity (e.g., are "bioactive") of a mammalian conservin protein are defined as polypeptides which includes an amino acid sequence corresponding (e.g., identical or homologous) to all or a portion of the amino acid sequences of a mammalian conservin proteins shown in any one or more of SEQ ID NOS:3 or 6 and which mimic or antagonize all or a portion of the biological/biochemical activities of a naturally occurring conservin protein. In preferred embodiments a conservin protein of the present invention specifically interacts with an FCHD534 polypeptide. Examples of such biological activity include the ability to induce (or otherwise modulate) formation and differentiation of tissue of developing mammalian embryos. Conservin proteins of the present invention can also have biological activities which include an ability to regulate organogensis, such as through the ability to influence limb patterning, by, for example, skeletogenic activity. Alternatively, conservin can be characterized by their ability to induce or inhibit the proliferation of such cells as fibroblasts, cells of the immune system, or smooth muscle cells. Additional effects of conservin may be seen on tissue maintenance and repair, such as bone repair or wound healing. The biological activity associated with conservin proteins of the present invention can also include the ability to modulate sexual maturity or reproduction, including functioning in regression of Mullerian ducts, modulating lactation or the production of follicle stimulating hormone, and spermatogenesis. The conservin proteins of the present invention can further be characterized by their role in modulation of tumorigenesis.

In preferred embodiments, a conservin protein can influence the proliferation of smooth muscle cells. In particularly preferred embodiments the subject polypeptides are capable of modulating the initiation and development of cardiovascular disease.

The bioactivity of the subject conservin proteins may also include the ability to alter the transcriptional rate of a gene, such as by participating in the transcriptional complexes (activating or inhibiting), e.g., either homo- or hetero-oligomeric in composition, or by altering the composition of a transcriptional complex by modfiying the competency and/or availability of proteins of the complex. The conservin gene products may also be involved in regulating post-translational modification of other cellular proteins, e.g., by action of an intrinsic enzymatic activity, or as a regulatory subunit of an enzyme complex, and/or as a chaperon.

Other biological activities of the subject conservin proteins are described herein or will be reasonably apparent to those skilled in the art. According to the present invention, a polypeptide has biological activity if it is a specific agonist or antagonist of a naturally-occurring form of a mammalian conservin protein.

The present invention further pertains to methods of producing the subject conservin polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant conservin polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant conservin polypeptide is a fusion protein containing a domain which facilitates its purification, such as GST fusion protein or poly(His) fusion protein.

Moreover, it will be generally appreciated that, under certain circumstances, it may be advantageous to provide homologs of one of the subject conservin polypeptides which function in a limited capacity as one of either a conservin agonist (mimetic) or a conservin antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of conservin proteins.

Homologs of each of the subject conservin proteins can be generated by mutagenesis, such as by discrete point mutation(s), or by truncation. For instance, mutation can give rise to homologs which retain substantially the same, or merely a subset, of the biological activity of the conservin polypeptide from which it was derived. Alternatively, antagonistic forms of the protein can be generated which are able to inhibit the function of the naturally occurring form of the protein, such as by competitively binding to a downstream or upstream member of the conservin cascade which includes the conservin protein. In addition, agonistic forms of the protein may be generated which are constituatively active. Thus, the mammalian conservin protein and homologs thereof provided by the subject invention may be either positive or negative regulators of signal transduction by TGF$\beta$'s.

The recombinant conservin polypeptides of the present invention also include homologs of the authentic conservin proteins, such as versions of those protein which are resistant to proteolytic cleavage, as for example, due to mutations which alter ubiquitination or other enzymatic targeting associated with the protein.

Conservin polypeptides may also be chemically modified to create conservin derivatives by forming covalent or aggregate conjugates with other chemical moieties, such as glycosyl groups, lipids, phosphate, acetyl groups and the like. Covalent derivatives of conservin proteins can be prepared by linking the chemical moieties to functional groups on amino acid sidechains of the protein or at the N-terminus or at the C-terminus of the polypeptide.

Modification of the structure of the subject mammalian conservin polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the conservin polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W. H. Freeman and Co.: 1981). Whether a change in the amino acid sequence of a peptide results in a functional conservin homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. polypeptides in which more than one replacement has taken place can readily be tested in the same manner.

This invention further contemplates a method for generating sets of combinatorial mutants of the subject conservin proteins as well as truncation mutants, and is especially useful for identifying potential variant sequences (e.g. homologs) that are functional in modulating signal transduction from a TGF receptor. The purpose of screening such combinatorial libraries is to generate, for example, novel conservin homologs which can act as either agonists or antagonist, or alternatively, possess novel activities all together. To illustrate, conservin homologs can be engineered by the present method to provide selective, constitutive activation of a TGF$\beta$ pathway, so as mimic signaling via a TGF$\beta$ pathway when the conservin homolog is expressed in a cell capable of responding to the TGF$\beta$. Thus, combinatorially-derived homologs can be generated to have an increased potency relative to a naturally occurring form of the protein.

Likewise, conservin homologs can be generated by the present combinatorial approach to selectively inhibit (antagonize) induction by a TGF$\beta$. For instance, mutagenesis can provide conservin homologs which are able to bind other signal pathway proteins (or DNA) yet prevent propagation of the signal, e.g. the homologs can be dominant negative mutants. Moreover, manipulation of certain domains of conservin by the present method can provide domains more suitable for use in fusion proteins.

In one embodiment, the variegated library of conservin variants is generated by combinatorial mutagenesis at the nucleic acid level, and is encoded by a variegated gene library. For instance, a mixture of synthetic oligonucleotides can be enzymatically ligated into gene sequences such that the degenerate set of potential conservin sequences are expressible as individual polypeptides, or alternatively, as a set of larger fusion proteins (e.g. for phage display) containing the set of conservin sequences therein.

There are many ways by which such libraries of potential conservin homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential conservin sequences. The synthesis of degenerate oligonucleotides is well known in the art (see for example, Narang, S. A. (1983) *Tetrahedron* 39:3; Itakura et al. (1981) *Recombinant DNA, Proc 3rd Cleveland Sympos. Macromolecules,* ed. A. G. Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.*

11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a conservin clone in order to generate a variegated population of conservin fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a conservin coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of conservin homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate conservin sequences created by combinatorial mutagenesis techniques.

In one embodiment, cell based assays can be exploited to analyze the variegated conservin library. For instance, the library of expression vectors can be transfected into a cell line ordinarily responsive to a particular TGFβ. The transfected cells are then contacted with the TGFβ and the effect of the conservin mutant on signaling by TGFβ can be detected, e.g. by measuring 3[H]Thymidine incorporation. Plasmid DNA can then be recovered from the cells which score for inhibition, or alternatively, potentiation of TGFβ induction, and the individual clones further characterized.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevir Publishing Co., Amsterdam, pp. 401–410; Delgrave et al., 1993, *Protein Engineering* 6(3):327–331).

The invention also provides for reduction of the mammalian conservin proteins to generate mimetics, e.g. peptide or non-peptide agents, which are able to interrupt binding of a mammalian conservin polypeptide of the present invention with either upstream or downstream components of a TGFβ signaling cascade, such as binding proteins or interactors. Thus, such mutagenic techniques as described above are also useful to map the determinants of the conservin proteins which participate in protein-protein interactions involved in, for example, binding of the subject mammalian conservin polypeptide to proteins which may function upstream (including both activators and repressors of its activity) or to proteins or nucleic acids which may function downstream of the conservin polypeptide, whether they are positively or negatively regulated by it, for example, the FCHD534 gene product. To illustrate, the critical residues of a subject conservin polypeptide which are involved in molecular recognition of, for example, the FCHD534 gene product or other component upstream or downstream of a conservin can be determined and used to generate conservin-derived peptidomimetics which competitively inhibit binding of the authentic conservin protein with that moiety. By employing, for example, scanning mutagenesis to map the amino acid residues of each of the subject conservin proteins which are involved in binding other extracellular proteins, peptidomimetic compounds can be generated which mimic those residues of the conservin protein which facilitate the interaction. Such mimetics may then be used to interfere with the normal function of a conservin protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

4.4.1. Cells expressing recombinant conservin polypeptides

This invention also pertains to a host cell transfected to express a recombinant form of the subject conservin polypeptides. The host cell may be any prokaryotic or eukaryotic cell. Thus, a nucleotide sequence derived from the cloning of mammalian conservin proteins, encoding all or a selected portion of the full-length protein, can be used to produce a recombinant form of a mammalian conservin polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinase, p53, WT1, PTP phosphatases, SRC, and the like. Similar procedures, or modifications thereof, can be employed to prepare recombinant conservin polypeptides by microbial means or tissue-culture technology in accord with the subject invention.

The recombinant conservin genes can be produced by ligating nucleic acid encoding a conservin protein, or a portion thereof, into a vector suitable for expression in either prokaryotic cells, eukaryotic cells, or both. Expression vectors for production of recombinant forms of the subject conservin polypeptides include plasmids and other vectors. For instance, suitable vectors for the expression of a conservin polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression,* ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a conservin polypeptide is produced recombinantly utilizing an expression vector generated by sub-cloning the coding sequence of one of the conservin genes represented in SEQ ID NOS:1, 2, 4 and 5.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press: 1989) Chapters 16 and 17.

In some instances, it may be desirable to express the recombinant conservin polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a conservin protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAp). MAP has been cloned from *E. coli* (Ben-Bassat et al. (1987) *J Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing conservin-derived polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below could be used to produce recombinant proteins.

4.4.2 Fusion proteins and Immunogens

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a conservin protein. For example, the VP6 capsid protein of rotavirus can be used as an immunologic carrier protein for portions of the conservin polypeptide, either in the monomeric form or in the form of a viral particle. The nucleic acid sequences corresponding to the portion of a subject conservin protein to which antibodies are to be raised can be incorporated into a fusion gene construct which includes coding sequences for a late vaccinia virus structural protein to produce a set of recombinant viruses expressing fusion proteins comprising conservin epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a conservin protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J Virol.* 62:3855; and Schlienger et al. (1992) *J. Virol.* 66:2).

The Multiple Antigen Peptide system for peptide-based immunization can also be utilized to generate an immunogen, wherein a desired portion of a conservin polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of conservin proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the mammalian conservin polypeptides of the present invention. For example, conservin polypeptides can be generated as glutathione-S-transferase (GST-fusion) proteins. Such GST-fusion proteins can enable easy purification of the conservin polypeptide, as for example by the use of glutathione-derivatized matrices (see, for example, *Current Protocols in Molecular Biology,* eds. Ausubel et al. (New York: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

4.4.3. Antibodies

Another aspect of the invention pertains to an antibody specifically reactive with a mammalian conservin protein. For example, by using immunogens derived from a conservin protein, e.g. based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a mammalian conservin polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a conservin protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a conservin protein of a mammal, e.g. antigenic determinants of a protein represented by SEQ ID NOS:3 or 6 or closely related homologs (e.g. at least 92% homologous, and more preferably at least 94% homologous).

Following immunization of an animal with an antigenic preparation of a conservin polypeptide, anti-conservin antisera can be obtained and, if desired, polyclonal anti-conservin antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4:72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a mammalian conservin polypeptide of the present invention and monoclonal antibodies isolated from a culture comprising such hybridoma cells. In one embodiment anti-human conservin I and conservin2 antibodies specifically react with the proteins encoded by the DNA of ATCC deposit 98049 or 98048.

The term antibody as used herein is intended to include fragments thereof which are also specifically reactive with one of the subject mammalian conservin polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a conservin protein conferred by at least one CDR region of the antibody.

Antibodies which specifically bind conservin epitopes can also be used in immunohistochemical staining of tissue samples in order to evaluate the abundance and pattern of expression of each of the subject conservin polypeptides. Anti-conservin antibodies can be used diagnostically in immuno-precipitation and immuno-blotting to detect and evaluate conservin protein levels in tissue as part of a clinical testing procedure. For instance, such measurements can be useful in predictive valuations of the onset or progression of proliferative disorders. Likewise, the ability to monitor conservin protein levels in an individual can allow determination of the efficacy of a given treatment regimen for an individual afflicted with such a disorder. The level of conservin polypeptides may be measured from cells in bodily fluid, such as in samples of cerebral spinal fluid or amniotic fluid, or can be measured in tissue, such as produced by biopsy. Diagnostic assays using anti-conservin antibodies can include, for example, immunoassays designed to aid in early diagnosis of a degenerative disorder, particularly ones which are manifest at birth. Diagnostic assays using anti-conservin polypeptide antibodies can also include immunoassays designed to aid in early diagnosis and phenotyping neoplastic or hyperplastic disorders.

Another application of anti-conservin antibodies of the present invention is in the immunological screening of cDNA libraries constructed in expression vectors such as λ gt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a conservin protein, e.g. other orthologs of a particular conservin protein or other paralogs from the same species, can then be detected with antibodies, as, for example, reacting nitrocellulose filters lifted from infected plates with anti-conservin antibodies. positive phage detected by this assay can then be isolated from the infected plate. Thus, the presence of conservin homologs can be detected and cloned from other animals, as can alternate isoforms (including splicing variants) from humans.

4.5 Methods of Treating Disease

There are a wide variety of pathological cell proliferative conditions for which conservin therapeutics of the present invention can be used in treatment. For instance, such agents can provide therapeutic benefits where the general strategy being the inhibition of an anomalous cell proliferation. Diseases that might benefit from this methodology include, but are not limited to various cancers and leukemias, psoriasis, bone diseases, fibroproliferative disorders such as those involving connective tissue, atherosclerosis, restenosis and other smooth muscle proliferative disorders, as well as chronic inflammation. In particular it is anticipated that mutation or deletion of both alleles of the subject conservin genes may lead to aberrant proliferation., i.e. the conservin may function as tumor suppressor genes. In addition to proliferative disorders, the present invention contemplates the use of conservin therapeutics for the treatment of differentiative disorders which result from, for example, de-differentiation of tissue which may (optionally) be accompanied by abortive reentry into mitosis, e.g. apoptosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

It will also be apparent that, by transient use of modulators of conservin pathways, in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For instance, conservin agonists and antagonists can be employed in a differential manner to regulate different stages of organ repair after physical, chemical or pathological insult. For example, such regimens can be utilized in repair of cartilage, increasing bone density, liver repair subsequent to a partial hepatectomy, or to promote regeneration of lung tissue in the treatment of emphysema.

Another aspect of the present invention relates to a method of inducing and/or maintaining a differentiated state, enhancing survival, and/or promoting (or alternatively inhibiting) proliferation of a cell responsive to a TGF-β factor, by contacting the cells with an agent which modulates conservin-dependent signaling by the growth factor. For instance, it is contemplated by the invention that, in light of the present finding of an apparently broad involvement of conservin proteins in the formation of ordered spatial arrangements of differentiated tissues in mammalians, the subject method could be used to generate and/or maintain an array of different mammalian tissue both in vitro and in vivo. A "conservin therapeutic," whether inductive or anti-inductive with respect to conservin by a TGF-β, can be, as appropriate, any of the preparations described above, including isolated polypeptides, gene therapy constructs, antisense molecules, peptidomimetics or agents identified in the drug assays provided herein.

In preferred embodiments a conservin protein of the present invention can modulate the development and/or progression of cardiovascular disease. For example, the compositions and methods of the present invention may be used to treat atherosclerosis, ischemia/reperfusion injuries, hupertension, and/or restinosis.

Since, in some cases, genes may be upregulated in a disease state and in other cases may be downregulated, it will be desirable to activate and/or potentiate or suppress and/or downmodulate conservin bioactivity depending on the condition to be treated using the techniques compounds and methods described herein. Some genes may be under-expressed in certain disease states. Several genes are now known to be down-regulated in monocytes under disease conditions. For example, bcl-2 and glutathione peroxidase gene expression is down-regulated in the monocytes of patients exposed to a high lipid diet, e.g cholesterol or fat, that leads to high serum LDL levels. The activity of conservin gene products may be in some way impaired, leading to the development of cardiovascular disease symptoms. Such down-regulation of conservin gene expression or decrease in the activity of a conservin protein may have a causative or exacerbating effect on the disease state.

Among the approaches which may be used to ameliorate disease symptoms involving the misexpression of a conservin gene are, for example, antisense, ribozyme, and triple helix molecules described above. Compounds that compete with an conservin protein for binding to upstream or downstream elements in a TGFβ signaling cascade will antagonize a conservin protein, thereby inducing a therapeutic effect. Examples of suitable compounds include the antagonists or homologues described in detail above. In other instances, the increased expression or bioactivity of a conservin protein may be desirable and may be accomplished by, for example the use of the conservin agonists or mimetics or by gene replacement therapy, as described herein.

Compounds identified as increasing or decreasing conservin gene expression or protein activity can be administered to a subjeat at therapeutically effective dose to treat or ameliorate cardiovascular disease. A therapeutically effective dose refers to that amount of the compound sufficient to result in amelioration of symptoms of cardiovascular disease.

4.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences,* Meade publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic conservin gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A mammalian conservin gene, such as any one of the sequences represented in the group consisting of SEQ ID NO:1 or 3, or a sequence homologous thereto can be delivered in a gene therapy construct by electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.6 Diagnostic and prognostic Assays

In the diagnostic and prognostic assays described herein, in addition to the conservin nucleic acid molecules and polypeptides described above, the present invention provides for the use of nucleic comprising at least a portion of the nucleic acid sequence shown in SEQ ID NO:5 or polypeptides comprising at least a portion of the amino acid sequence shown in SEQ ID NO:6.

The present method provides a method for determining if a subject is at risk for a disorder characterized by aberrant cell proliferation and/or differentiation. In preferred embodiments, the methods can be characterized as comprising detecting, in a sample of cells from the subject, the presence or absence of a genetic lesion characterized by at least one of (i) an alteration affecting the integrity of a gene encoding a conservin-protein, or (ii) the mis-expression of the conservin gene. To illustrate, such genetic lesions can be detected by ascertaining the existence of at least one of (i) a deletion of one or more nucleotides from a conservin gene, (ii) an addition of one or more nucleotides to a conservin gene, (iii) a substitution of one or more nucleotides of a conservin gene, (iv) a gross chromosomal rearrangement of a conservin gene, (v) a gross alteration in the level of a messenger RNA transcript of a conservin gene, (vii) aberrant modification of a conservin gene, such as of the methylation pattern of the genomic DNA, (vii) the presence of a non-wild type splicing pattern of a messenger RNA transcript of a conservin gene, (viii) a non-wild type level of a conservin-protein, (ix) allelic loss of a conservin gene, and (x) inappropriate post-translational modification of a conservin-protein. As set out below, the present invention provides a large number of assay techniques for detecting lesions in a conservin gene, and importantly, provides the ability to discern between different molecular causes underlying conservin-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a conservin gene, such as represented by any of SEQ ID NOS:1, 2, 4, or 5, or naturally occurring mutants thereof, or 5' or 3' flanking sequences or intronic sequences naturally associated with the subject conservin genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

As set out above, one aspect of the present invention relates to diagnostic assays for determining, in the context of cells isolated from a patient, if mutations have arisen in one or more conservin of the sample cells. The present method provides a method for determining if a subject is at risk for a disorder characterized by aberrant cell proliferation and/or differentiation. In preferred embodiments, the method can be generally characterized as comprising detecting, in a sample of cells from the subject, the presence or absence of a genetic lesion characterized by an alteration affecting the integrity of a gene encoding a conservin. To illustrate, such genetic lesions can be detected by ascertaining the existence of at least one of (i) a deletion of one or more nucleotides from a conservin-gene, (ii) an addition of one or more nucleotides to a conservin-gene, (iii) a substitution of one or more nucleotides of a conservin-gene, and (iv) the presence of a non-wild type splicing pattern of a messenger RNA transcript of a conservin-gene. As set out below, the present invention provides a large number of assay techniques for detecting lesions in conservin genes, and importantly, provides the ability to discern between different molecular causes underlying conservin-dependent aberrant cell growth, proliferation and/or differentiation.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) PNAS 91:360–364), the latter of which can be particularly useful for detecting point mutations in the conservin-gene (see Abravaya et al. (1995) Nuc Acid Res 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a conservin gene under conditions such that hybridization and amplification of the conservin-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternative amplification methods include: self sustained sequence replication (Guatelli, J. C. et al., 1990, Proc. Natl. Acad. Sci. U.S.A. 87:1874–1878), transcriptional amplification system (Kwoh, D. Y. et al., 1989, Proc. Natl. Acad. Sci. U.S.A. 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in a conservin gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the conservin gene and detect mutations by comparing the sequence of the sample conservin with the corresponding wild-type (control) sequence. Exemplary sequencing reactions include those based on techniques developed by Maxim and Gilbert (Proc. Natl Acad Sci USA (1977) 74:560) or Sanger (Sanger et al (1977) Proc. Nat. Acad. Sci 74:5463). It is also contemplated that any of a variety of automated sequencing procedures may be utilized when performing the subject assays (Biotechniques (1995) 19:448), including by sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one skilled in the art that, for certain embodiments, the occurence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes of formed by hybridizing (labelled) RNA or DNA containing the wild-type conservin sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymod. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in conservin cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a conservin sequence, e.g., a wild-type conservin sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in conservin genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control conservin nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele speicific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol Cell probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Another embodiment of the invention provides for a nucleic acid composition comprising a (purified) oligonucleotide probe including a region of nucleotide sequence which is capable of hybridizing to a sense or antisense sequence of a conservin-gene, or naturally occurring mutants thereof, or 5' or 3' flanking sequences or intronic sequences naturally associated with the subject conservin-genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, neoplastic or hyperplastic disorders (e.g. aberrant cell growth).

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a conservin gene.

Any cell type or tissue, preferably monocytes, endothelial cells, or smooth muscle cells, in which the conservin is expressed may be utilized in the diagnostics described below. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, New York).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant conservin proteins, which are discussed, above, may also be used indisease diagnostics and prognostics. Such diagnostic methods, may be used to detect abnormalities in the level of conservin protein expression, or abnormalities in the structure and/or tissue, cellular, or subcellular location of conservin protein. Structural differences may include, for example, differences in the size, electronegativity, or antigenicity of the mutant conservin protein relative to the normal conservin protein. protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of conservin proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the conservin protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. preferred supports include polystyrene beads. Those skilled in the art will know many other suitable carriers for binding antibody or antigen, or will be able to ascertain the same by use of routine experimentation.

One means for labeling an anti-conservin protein specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly publication, Walkersville, Md.; Voller, et al., J. Clin. pathol. 31:507–520 (1978); Butler, Meth. Enzymol. 73:482–523 (1981); Maggio, (ed.) *Enzyme Immunoassay,* CRC Press, Boca Raton, Fla., 1980; Ishikawa, et al., (eds.) *Enzyme Immunoassay,* Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays,* Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a conservin gene or gene product can be used to monitor the course of treatment or therapy.

4.7. Drug Screening Assays

In drug screening assays described herein, in addition to the conservin nucleic acid molecules and polypeptides described above, the present invention also provides for the use of nucleic comprising at least a portion of the nucleic acid sequence shown in SEQ ID NO:5 or polypeptides comprising at least a portion of the amino acid sequence shown in SEQ ID NO:6.

Furthermore, by making available purified and recombinant conservin polypeptides, the present invention facilitates the development of assays which can be used to screen for drugs, including conservin homologs, which are either agonists or antagonists of the normal cellular function of the subject conservin polypeptides, or of their role in the pathogenesis of cellular differentiation and/or proliferation and disorders related thereto. In one embodiment, the assay evaluates the ability of a compound to modulate binding between a conservin polypeptide and a molecule, be it protein or DNA, that interacts either upstream or downstream of the conservin polypeptide in the TGFβ signaling pathway. A variety of assay formats will suffice and, in light of the present inventions, will be comprehended by a skilled artisan.

4.7.1 Cell-free assays

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity) or to proteins or nucleic acids which may function downstream of the conservin polypeptide, whether they are positively or negatively regulated by it. To the mixture of the compound and the upstream or downstream element is then added a composition containing a conservin polypeptide. Detection and quantification of complexes of conservin with it's upstream or downstream elements provide a means for determining a compound's efficacy at inhibiting (or potentiating) complex formation between conservin and the conservin-binding elements. The efficacy of the compound can be assessed by generating dose response curves from data obtained using various concentrations of the test compound. Moreover, a control assay can also be performed to provide a baseline for comparison. In the control assay, isolated and purified conservin polypeptide is added to a composition containing the conservin-binding element, and the formation of a complex is quantitated in the absence of the test compound.

Complex formation between the conservin polypeptide and a conservin binding element may be detected by a variety of techniques. Modulation of the formation of complexes can be quantitated using, for example, detectably labeled proteins such as radiolabeled, fluorescently labeled, or enzymatically labeled conservin polypeptides, by immunoassay, or by chromatographic detection.

Typically, it will be desirable to immobilize either conservin or its binding protein to facilitate separation of complexes from uncomplexed forms of one or both of the proteins, as well as to accommodate automation of the assay. Binding of conservin to an upstream or downstream element, in the presence and absence of a candidate agent, can be accomplished in any vessel suitable for containing the reactants. Examples include microtitre plates, test tubes, and micro-centrifuige tubes. In one embodiment, a fusion protein can be provided which adds a domain that allows the protein to be bound to a matrix. For example, glutathione-S-transferase/conservin (GST/conservin) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of conservin-binding protein found in the bead fraction quantitated from the gel using standard electrophoretic techniques such as described in the appended examples.

Other techniques for immobilizing proteins on matrices are also available for use in the subject assay. For instance, either conservin or its cognate binding protein can be immobilized utilizing conjugation of biotin and streptavidin. For instance, biotinylated conservin molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with conservin but which do not interfere with binding of upstream or downstream elements can be derivatized to the wells of the plate, and conservin trapped in the wells by antibody conjugation. As above, preparations of a conservin-binding protein and a test compound are incubated in the conservin-presenting wells of the plate, and the amount of complex trapped in the well can be quantitated. Exemplary methods for detecting such complexes, in addition to those described above for the GST-immobilized complexes, include immunodetection of complexes using antibodies reactive with the conservin binding element, or which are reactive with conservin protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the conservin-BP. To illustrate, the conservin-Bp can be chemically cross-linked or genetically fused with horseradish peroxidase, and the amount of polypeptide trapped in the complex can be assessed with a chromogenic substrate of the enzyme, e.g. 3,3'-diaminobenzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-conservin antibodies, can be used. Alternatively, the protein to be detected in the complex can be "epitope tagged" in the form of a fusion protein which includes, in addition to the conservin sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, New Jersey).

4.7.2. Cell based assays

In addition to cell-free assays, such as described above, the readily available source of mammalian conservin proteins provided by the present invention also facilitates the generation of cell-based assays for identifying small molecule agonists/antagonists and the like. For example, cells which are sensitive to TGFβ signals can be caused to overexpress a recombinant conservin protein in the presence and absence of a test agent of interest, with the assay scoring for modulation in conservin responses by the target cell mediated by the test agent. As with the cell-free assays, agents which produce a statistically significant change in conservin-dependent responses (either inhibition or potentiation) can be identified. In an illustrative embodiment, the expression or activity of a conservin is modulated embryos or cells and the effects of compounds of interest on the readout of interest (such as tissue differentiation, proliferation, tumorigenesis) are measured. For example, the expression of genes which are up- or down-regulated in response to a conservin-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected.

Exemplary cell lines may include non-recombinant monocyte cell lines, such as U937 (ATCC# CRL-1593), THP-1 (ATCC# TIB-202), and P388DI (ATCC# TIB-63); endothelial cells such as HUVEC's and bovine aortic endothelial cells (BAEC's); as well as generic mammalian cell lines such as HeLa cells and COS cells, e.g., COS-7 (ATCC# CRL-1651). Further, the transgenic animals discussed herein may be used to generate cell lines, containing one or more cell types involved in cardiovascular disease, that can be used as cell culture models for this disorder. While primary cultures derived from the cardiovascular disease transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

For example, the effect of a test compound on a variety of end points could be tested including rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα:, TNFα, HB-EGF, PDGF, IFN-γ, and GM-CSF. Similarly, HWVEC's can be treated with test compounds or transfected with genetically engineered conservin genes. The HUVEC's can then be examined for phenotypes associated with cardiovascular disease, including, but not limited to changes in cellular morphology, cell proliferation, cell migration, and mononuclear cell adhesion; or for the effects on production of other proteins involved in cardiovascular disease such as ICAM, VCAM, PDGF-β, and E-selectin.

In the event that the conservin proteins themselves, or in complexes with other proteins, are capable of binding DNA and modifying transcription of a gene, a transcriptional based assay could be used, for example, in which a conservin responsive regulatory sequence is operably linked to a detectable marker gene.

Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject conservin polypeptides can be used to generate a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with conservin ("conservin-binding proteins" or "conservin-bp"), such as FCHD 534, and the like. Such conservin-binding proteins would likely also be involved in the propagation of TGFβ signals by the conservin proteins as, for example, the upstream or downstream elements of the conservin pathway or as collateral regulators of signal bioactivity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a conservin polypeptide. The second hybrid protein encodes a transcriptional activation domain fused in frame to a sample gene from a cDNA library. If the bait and sample hybrid proteins are able to interact, e.g., form a conservin-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the conservin and sample proteins.

4.8 Transgenic animals

These systems may be used in a variety of applications. For example, the cell- and animal-based model systems may be used to further characterize conservin genes and proteins. In addition, such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

4.8.1. Animal-based systems

One aspect of the present invention concerns transgenic animals which are comprised of cells (of that animal) which contain a transgene of the present invention and which preferably (though optionally) express an exogenous conservin protein in one or more cells in the animal. A conservin transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a conservin protein can be essential for many forms of lineage analysis and can additionally provide a means to assess the effects of, for example, lack of conservin expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject conservin proteins. For example, excision of a target sequence which interferes with the expression of a recombinant conservin gene, such as one which encodes an antagonistic homolog or an antisense transcript, can be designed to activate expression of that gene. This interference with expression of the protein can result from a variety of mechanisms, such as spatial separation of the conservin gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant conservin protein can be regulated via control of recombinase expression.

Use of the cre/loxP recombinase system to regulate expression of a recombinant conservin protein requires the construction of a transgenic animal containing transgenes encoding both the Cre recombinase and the subject protein. Animals containing both the Cre recombinase and a recombinant conservin gene can be provided through the construction of "double" transgenic animals. A convenient method for providing such animals is to mate two transgenic animals each containing a transgene, e.g., a conservin gene and recombinase gene.

One advantage derived from initially constructing transgenic animals containing a conservin transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic conservin transgene is silent will allow the study of progeny from that founder in which disruption of conservin mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the conservin transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a conservin transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). preferred strains are those with $H-2^b$, $H-2^d$ or $H-2^q$ haplotypes such as C57BL/6 or DBA/1. The line(s) used to practice this invention may themselves be transgenics, and/or may be knock-outs (i.e., obtained from animals which have one or more genes partially or completely suppressed) .

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a conservin protein (either agonistic or antagonistic), and antisense transcript, or a conservin mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) et al. *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting a conservin gene of interest in ES cells, these changes can be introduced into the germlines of animals to generate chimeras. The gene targeting procedure is accomplished by introducing into tissue culture cells a DNA targeting construct that includes a segment homologous to a target conservin locus, and which also includes an intended sequence modification to the conservin genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a conservin gene function through the use of a targeting transgene construct designed to undergo homologous recombination with one or more conservin genomic sequences. The targeting construct can be arranged so that, upon recombination with an element of a conservin gene, a positive selection marker is inserted in to (or replaces) coding sequences of th e targeted singling gene. The inserted sequence functionally disrupts the conservin gene, while also providing a positive selection trait. Exemplary conservin targeting constructs are described in more detail below.

Generally, the embryonic stem cells (ES cells ) used to produce the knockout animals will be of the same species as the knockout animal to be generated. Thus for example, mouse embryonic stem cells will usually be used for gene ratio n of knockout mice.

Embryonic stem cells are gene rated and maintained using methods well known to the skilled artisan such as those described by Doetschman et al. (1985) *J. Embryol Exp. Morphol* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of in sertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the conservin coding sequence, transcriptional regulatory sequence, etc.

Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the conservin gene knocked out in various tissues of the offspring by probing the Western blot with an antibody against the particular conservin protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a conservin-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

5. EXAMPLES

5.1 Identification of conservin genes

Yeast strains, Media, and Microbiological Techniques

Yeast strains, *E. coli* strains, and plasmids used in this work are listed in Table 1. Standard yeast media including synthetic complete medium lacking L-leucine, L-typtophan, and L-histidine were prepared and yeast genetic manipulations were performed as described (Sherman, 1991, Meth. Enzymol., 194:3–21). Yeast transformations were performed using standard protocols (Gietz et al., 1992, Nucleic Acids Res., 20:1425. Ito et al, 1983, J. Bacteriol., 153:163–168). Plasmid DNAs were isolated from yeast strains by a standard method (Hoffman and Winston, 1987, Gene, 57:267–272).

TABLE 1

| Strain | Genotype | Source or Derivation |
|---|---|---|
| *E. Coli* | | |
| PEB199 | F- ompT hsd$S_B$ ($r_B^- m_B^-$) gal dcm lon | BL21 lon (Studier, 1991 J. Mol. Biol., 219:37–44.) derivative obtained from G. Walker |
| E1 | PBB199 + pMB118 | This study |
| Yeast | | |
| HF7c | MATα ura3–52 his3–200 lys2–801 ade2–101 trp1–901 leu2–3,112 gal4–542 gal80–538 LYS2::GAL1$_{UAS}$—GAL$_{TATA}$—HIS3 URA3::GAL4$_{17mers(x3)}$—CyC1$_{TATA}$—lacZ | (Feilotter et al., 1994, Nucleic Acids Res. 22:1502–1503.) |
| Y187 | MATα gal4 gal80 his3 trp1–901 ade2–101 ura3–52 leu2–3, 112 met- URA3::GAL-->lacZ | (S. J. Elledge, personal communication) |
| MY114 | HF7c + pYCHD534b | This study |
| TB29 | HF7c + pYCHX01 | This study |
| TB32 | HF7c + pYCFX011 | This study |
| Plasmid Name | Description | Source or Derivation |
| pACTII | GAL4(768–881) fusion vector | (S. J. Elledge, personal communication) |

TABLE 1-continued

| | | |
|---|---|---|
| pGBT9 | GAL4(1–147) fusion vector marked with TRP1 and amp$^r$ | (Bartel et al., 1993, Cellular Interactions in Development. 153–159.) |
| pYCHD534b | 534 coding sequence cloned in frame into pGBT9 | This study |
| pYCFX011 | Drosophila MAD coding sequence cloned in frame into pGBT9 | This study |
| pYCHX01 | DPC4 coding sequence cloned into frame into pGBT9 | This study |
| pGEX-4T-1 | GST gene fusion vector | Pharmacia Biotech Catalogue |
| pMB118 | conservin1 coding sequence cloned in pGEX-4t-1 | This study |
| p12b1 | conservin1 in pACTII | This study |
| p15c2 | conservin2 in pACTII | This study | plasmid Construction p12B1 and p15C2 were isolated in a two-hybrid screen from an oligo-dT primed human breast cDNA library constructed in the lambda ACTII vector and then converted to a pACTII-based library.

The coding region of the Drosophila MAD (Sekelsky et al., 1995, Genetics, 139:1347) was amplified by PCR and cloned in frame into pGBT9 resulting in plasmid pYCFX011. pYCFX011 was transformed into two-hybrid screening strain HF7c and one resulting transformant was designated TB32.

The coding region of the DCP4 (Hahn et al., 1996 Science, 271:350) was amplified by PCR and cloned in frame into pGBT9 resulting in plasmid pYCHX01. pTCHX01 was transformed into two-hybrid screening strain HF7c and one resulting transformant was designated TB29.

pGBT9–12 was doubly digested with EcoRI and SalI and the approximately 440 bp fragment encoding conservin1 protein was cloned into EcoRI and SAlI digested pGEX-4T-1. DNA sequencing of one of the resulting clones designated pMB118 verified the fusion junction. pMB118 was transformed into GST-fusion expression strain pEB199 and one resulting transformant was designated E1.

Two-Hybrid Screen with 534

The following primers were used to amplify the coding region of the FCHD534 cDNA: CGGGATCCGTGCTGCT-GCTATGTCCAGAATGGGCAAACCCAT (SEQ ID. NO:9) and ACTGTCGACCTATCTGGGGTTGTTGT-TGAGGAGGAT (SEQ ID. NO:10). Restriction endonuclease sites BamHI and SalI were engineered into the oligonucleotides to allow the cloning of the FCHD534 gene into two-hybrid system DNA-binding domain fusion vector pGBT9 (Clontech, Palo Alto, Calif.). Fchd534 was cloned in frame into pGBT9 by digesting the PCR product with BamHI and SalI and ligating it into BamHI and SalI digested pGBT9. DNA sequencing of one of the resulting clones, designated YCHD534b, verified the fusion junction and the sequence of the Fchd534 coding sequence insert. Clone YCHD534b was transformed into two-hybrid screening strain HF7c (Clontech; Palo Alto, Calif.) One resulting transformant was selected and designated MY114.

Western Blotting

A total protein extract of MY 114 was subjected to Western blotting analysis to confirm and qualitatively evaluate expression of the GAL4 DNA-binding domain FCHD534 fusion protein. The protein extract was prepared by growing MY114 in synthetic complete medium lacking L-tryptophan (Sherman. 1991. Meth. Enzymol. 194:3) to an $OD_{600}$ of 1. The yeast cells from 4.5 ml of culture were collected by centrifugation and the cell pellet was resuspended in 1 ml of 0.25M NaOH 1% beta-mercaptoethanol and incubated at 4° C. for 10 minutes. 160 $\mu$l of 50% TCA were then added to the cell suspension and after mixing the suspension was incubated at 4° C. for 10 minutes. The suspension was then microfuged at 4° C. for 10 minutes, the supernatant fraction was discarded, and the pellet was washed with cold acetone, air dried, and then resuspended in 120 $\mu$l of 2× tris-glycine SDS sample buffer (Novex, San Diego, Calif.) diluted to 1× strength with deionized water. 15 $\mu$l of the sample was boiled for 2 minutes and then electrophoresed on a 14% tris glycine SDS polyacrylamide gel (Novex) and then transferred to an immobilon PVDF membrane (Millipore; San Francisco, Calif.). The primary antibody utlized was a rabbit anti-yeast GAL4 DNA-binding domain polyclonal antibody (Upstate Biotechnology Inc.; Lake placid, N.Y.) and the secondary antibody was a donkey anti-rabbit Ig, peroxidase linked species-specific whole antibody (Amersham Life Science; Cleveland, Ohio). Western blotting procedures were essentially as described (Sambrook et al. Molecular Cloning 2nd edition. Cold Spring Harbor Laboratory Press. 1989) and proteins interacting with the antibodies were visualized using the ECL detection system (Amersham Life Sciences), essentially as described by the manufacturer. Expression of the GAL4 DNA-binding domain FCHD534 fusion protein was detected.

Two-hybrid screening

Two-hybrid screening was carried out essentially as described (Clonetech) using MY114 as the recipient strain and a human breast two-hybrid library constructed in the lambda ACT II vector. 4×10$^6$ transformants were obtained and 111 yeast colonies that both grew on synthetic complete medium lacking L-leucine, L-tryptophan, and L-histidine and expressed the beta-galactosidase reporter gene were identified. The 52 strains with the strongest beta-galactosidase induction were further characterized. Library plasmids were isolated from the 52 strains using a standard method (Hoffman and Winston. 1987. Gene 57:267), and the 5' ends of all of the cDNA inserts were sequenced. Nine library plasmids were discarded because of obvious artifacts, and the remaining 43 plasmids were found to represent 19 different cDNAs. Two cDNAs were selected for further testing, conservin1 and conservin2.

Retransformation and specificity testing of, conservin1 and conservin2

It was confirmed that conservin1 and conservin2 cDNAs encode proteins that physically interact specifically with FCHD534. Yeast expression plasmids encoding GAL4 DNA-binding domain fusions to 534, MAD, DCP4, and p53 as a control were transformed into MATa two-hybrid screening strain HF7c. Yeast expression plasmids encoding GAL4 activation domain fusions to, conservin1, conservin2, and SV40 as a control were transformed into MATα two-hybrid screening strain Y187. p53 and SV40 interact with each other and should not interact with the experimental proteins. The HF7c transformant were propagated as stripes on semi-solid synthetic complete medium lacking L-tryptophan and the Y187 transformants were grown as stripes on semisolid synthetic complete medium lacking L-leucine. Both sets of stripes were replica plated in the form of a grid onto a single rich YPAD plate and the haploid strains of opposite mating types were allowed to mate overnight at 30° C. The yeast strains on the mating plate were then replica plated to a synthetic complete plate lacking L-leucine and L-tryptophan to select for diploids and incubated at 30° C. overnight. Diploid strains on the synthetic complete plate lacking L-leucine and L-tryptophan were replica plated to a synthetic complete plate lacking L-leucine, L-tryptophan, and L-histidine to assay HIS3 expression and a paper filter on a synthetic complete plate lacking L-leucine and L-tryptohan. The next day the paper filter was subjected to the paper filter beta-galactosidase assay to measure expression of the lacZ reporter gene. HIS3 expression was scored after 3 days of growth at 30° C. The results are summarized in the table below.

Summary of Retransformation and Specificity Tests

| GAL4 DNA-Binding Domain | cDNA-GAL4 Activation Domain Fusion Being tested | | |
|---|---|---|---|
| Fusions | conservin1 | conservin2 | SV40 |
| 534 | Strong | Strong | None |
| MAD | None | None | None |
| DPC4 | None | None | None |
| p53 | None | None | Strong |

The strength or absence of physical interaction between each combination of test proteins is listed. Strong interactions are defined as interactions that cause the activation of both the HIS3 and lacZ reporter genes. Northern Analysis The probes were prepared by combining 2 μl of 1 kb EcoRI/BamHI digested cDNA-1 (~30 ng), 7 μl of H$_2$0, and 2 μl of 10× Hexanucleotide mix (Boehringer; Indianapolis, Ind.). The mixture was heated to 95° 5 min and then cooled on ice. Subsequently, 3 μl of dATP/dGTP/dTTP mix (1:1:1 of 0.5 mM each), 5 μl of α32P dCTP 3000 Ci/mM (50 uCi total) (Amersham ; Arlington Heights, Ill.), and 1 μl of Klenow fragment (2 units) (Boehringer). The mixture was incubated at 37° for 1 hr. 30 μl TE was then added and the probe was spun on a Biospin 6 column (Biorad; Hercules, Calif.). 1 μl of eluate was measured for incorporation of nucleotide in a scintillation counter with scintillant.

One percent gels were prepared in MOPS buffer using standard procedures. Briefly, 3 g of agarose (Seakem LE; Rockland, Me.), 60 ml 5× MOPS buffer, and 210 ml of sterile H$_2$0 were combined. Gels were run with ethidium bromide and fomaldehyde. RNA loading dyes were added to RNA samples to 1× final concentration. Sampels were heated to 65° for 5 min. and cooled on ice before loading gel. Generally, gels were run for 6 hrs. or overnight in 1× MOPS buffer. 10 μg of RNA MW standards were also denatured with dye and loaded on to gel, following standard protocols.

For blotting, gels were soaked in 50 mM NaOH, 0.1M NaCl for 30 min. with shaking, then in 0.1M Tris-HCL pH 8.0 for 30 min., then were transferred to 20× SSC for 20 min. Gels were then blotting using Hybond-N membrane (nylon, Amersham) according to standard protocols in 20× SCC overnight. RNA was crosslixed to the membrane using Stratalinker (La Jolla, Calif.).

For hybridization, blots were placed into roller bottle containing 10 ml of rapid-hyb solution (Amersham), and pre-hybridized for at least 1 hr. at 65°. 1×10$^7$ cpm of probe was heated to 95°, chilled on ice and added to 10 ml of hybridization solution and hybridized with the blot at 65° for 3 hrs.

For washing, the first wash was done for 20 min. in 2× SSC/0.1% SDS, room temperature, the second for 15 min. in 0.1×SSC/0.1% SDS, at 65° before being covered in plastic wrap and put down for exposure.

A 1 kb band was observed based on Northern Blot analysis of RNA prepared from most human tissues and human umbilical vein endothelial cells (Clonetech) using a 1 kb probe of conservin012 subcloned into the pCINeo expression vector (promega; Madison, Wis.) in the sense and antisense orientations for generating messages in mammalian cells.

Beta Galactosidase Assays

The filter disk beta-galactosidase (beta-gal) assay was performed essentially as previously described (Brill et al., 1994, Mol. Biol. Cell, 5:297–312.). Briefly, strains to be tested were grown as patches of cells on appropriate medium dictated by the experiment at 30° C. overnight. The patches or colonies of cells were replica plated to Whatman #50 paper disks (Schleicher & Schuell, #576; Keene, N.H.) that had been placed on the test medium in petri dishes. After growth overnight at 30° C., the paper disks were removed from the plates and the cells on them were permeabilized by immediately immersing them in liquid nitrogen for 30 seconds. After this treatment, the paper disks were thawed at room temperature for 20 seconds and then placed in petri dishes that contained a disk of Whatman #3 paper (Schleicher & Schuell, #593) saturated with 2.5 ml of Z buffer containing 37 μl of 2% weight per volume of the chromogenic beta-gal substrate X-gal. The permeabilized strains on the paper disks were incubated at 30° C. and inspected at timed intervals for the blue color diagnostic of beta-gal activity in this assay. The assay was stopped by removing the paper disk containing the patches of cells and air drying it.

Expression andpurification of recombinant proteins

An overnight culture of E. coli strain E1 carrying the pMB118 conservin1 GST-fusion plasmid was grown overnight in TB 100 μg/ml ampicillin medium. The following day the culture was diluted 1:10 in fresh TB 100 μg/ml ampicillin medium and grown to an OD600 of 0.6–0.8. IPTG was added to the culture to a final concentration of 0.5–1.0 mM and the culture was then incubated for 3–4 hours at 37° C. The culture was pelleted and stored frozen (−80° C.) for 1 day. The culture was thawed and resuspended in 20–50 ml of PBS and passed through a French press 2–3 times at 20,000 psi. Disruption was monitored by taking OD 600 readings of the lysate. The lysate was centrifuged for 30 min. at 15,000×g and the supernatant was decanted to a fresh tube. Glutathione Sepharose 4B resin (Pharmacia Biotech; Piscataway, N.J.) was washed with 5–10 column volumes of PBS to remove resin storage buffer. The supernatant was added to the washed resin. The resulting slurry was added to a 50 ml conical tube and batch binding was allowed to proceed for one hour. The slurry was washed twice with 10 column volumes of PBS and then the recombinant protein was eluted with a 50 mM tris-HCl pH 8.0 buffer containing 50 mM reduced glutathione. Eluted proteins were analyzed by electrophoresis on a 14% tris glycine SDS polyacrylamide gel (Novex) and subsequent Coomassie staining.

The fusion protein is predicted to be 43 kd in molecular weight because conservin1 is predicted to be 17 kd and GST is 26 kd. IPTG induction of recombinant protein expression in PEB199 transformed with the GST-conservin1 construct resulted in the production of 43 kd fusion protein as determined by polyacrylamide gel electrophoretic analysis of the proteins purified from a lysate of this induced *E. coli* strain using glutathione beads.

Deposit of Microorganisms conservin1 and conservin2 were deposited with the American Type Culture Collection Rockville, Md., on May 8, 1996 under the terms of the Budapest Treaty and assigned accession numbers 98049 and 98048, respectively.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated nucleic acid molecule comprising a nucleotide sequence encoding a polypeptide which is at least 92.5% identical to the amino acid sequence of SEQ ID NO:3 or 6 and which binds in a yeast two hybrid assay with the polypeptide encoded by the fchd 534 gene deposited with NRRL as Accession Number B-21458.

2. The nucleic acid molecule of claim 1, wherein the polypeptide comprises the amino acid sequence of SEQ ID NO:3 or 6.

3. The nucleic acid molecule of claim 1, wherein the nucleotide sequence is at least 75% identical to the nucleotide sequence of SEQ ID NO:1 or 4.

4. The nucleic acid molecule of claim 3, wherein the nucleotide sequence is at least 80% identical to the nucleotide sequence of SEQ ID NO:1 or 4.

5. The nucleic acid molecule of claim 4, wherein the nucleotide sequence is at least 90% identical to the nucleotide sequence of SEQ ID NO:1 or 4.

6. The nucleic acid molecule of claim 5, which comprise the nucleotide sequence of SEQ ID NO:1 or 4.

7. An isolated nucleic acid molecule comprising a nucleotide sequence encoding a polypeptide which is at least 92.5% identical to the amino acid sequence encoded by the nucleotide sequence of the human DNA insert of the plasmid deposited with ATCC® as Accession Number 98048 or 98049 and which binds in a yeast two hybrid assay with the polypeptide encoded by the fchd 534 gene deposited with NRRL as Accession Number B-21458.

8. The nucleic acid molecule of claim 7, wherein the polypeptide comprises the amino acid sequence encoded by the nucleotide sequence of the human DNA insert of the plasmid deposited with ATCC® as Accession Number 98048 or 98049.

9. The nucleic acid molecule of claim 7, wherein the nucleotide sequence is at least 75% identical to the nucleotide sequence of the human DNA insert of the plasmid deposited with ATCC® as Accession Number 98048 or 98049.

10. The nucleic acid molecule of claim 9, wherein the nucleotide sequence is it least 80% identical to the nucleotide sequence of the human DNA insert of the plasmid deposited with ATCC® as Accession Number 98048 or 98049.

11. The nucleic acid molecule of claim 10, wherein the nucleotide sequence is at least 90% identical to the nucleotide sequence of the human DNA insert of the plasmid deposited with ATCC® as Accession Number 98048 or 98049.

12. The nucleic acid molecule of claim 11, wherein the which comprises the nucleotide sequence of the human DNA insert of the plasmid deposited with ATCC® as Accession Number 98048 or 98049.

13. An isolated nucleic acid molecule comprising a nucleotide sequence which is at least 75% identical to the nucleotide sequence of SEQ ID NO:1 or 4.

14. The nucleic acid molecule of claim 13, wherein the nucleotide sequence is at least 80% identical to the nucleotide sequence of the SEQ ID NO:1 or 4.

15. The nucleic acid molecule of claim 14, wherein the nucleotide sequence is at least 90% identical to the nucleotide sequence of SEQ ID NO:1 or 4.

16. An isolated nucleic acid molecule comprising a nucleotide sequence is at least 75% identical to the nucleotide sequence of the human DNA insert of the plasmid deposited with ATCC® as Accession Number 98048 or 98049.

17. The nucleic acid molecule of claim 16, wherein the nucleotide sequence is at least 80% identical to the nucleotide sequence of the human DNA insert of the plasmid deposited with ATCC® as Accession Number 98048 or 98049.

18. The nucleic acid molecule of claim 17, wherein the nucleotide sequence is at least 90% identical to the nucleotide sequence of the human DNA insert of the plasmid deposited with ATCC® as Accession Number 98048 or 98049.

19. An isolated nucleic acid molecule comprising a nucleotide sequence which is complementary to the nucleotide sequence of the nucleic acid molecule as in claim 1, 2, 3, 4, 5, 13, 14, or 15.

20. The nucleic acid molecule as in claim 1, 2, 3, 4, 5, 13, 14, or 15, which is genomic DNA.

21. The nucleic acid molecule as in claim 1, 2, 3, 4, 5, 13, 14, or 15, which is cDNA.

22. The nucleic acid molecule as in claim 1, 2, 3, 4, 5, 13, 14, or 15, which is RNA.

23. A vector comprising the nucleic acid molecule as in claim 1, 2, 3, 4, 5, 13, 14, or 15.

24. The vector of claim 23, which is a recombinant expression vector.

25. A host cell containing the vector of claim 23.

26. A host cell containing the recombinant expression vector of claim 24.

27. An isolated nucleic acid molecule comprising a nucleotide sequence which is complementary to the nucleotide sequence of the nucleic acid molecule as in claim 7, 8, 9, 10, 11, 6, 12, 16, 17, or 18.

28. The nucleic acid molecule as in claim 7, 8, 9, 10, 11, 6, 12, 16, 17, or 18, which is genomic DNA.

29. The nucleic acid molecule as in claim 7, 8, 9, 10, 11, 6, 12, 16, 17, or 18, which is cDNA.

30. The nucleic acid molecule as in claim 7, 8, 9, 10, 11, 6, 12, 16, 17, or 18, which is RNA.

31. A vector comprising the nucleic acid molecule as in claim 7, 8, 9, 10, 11, 6, 12, 16, 17, or 18.

32. The vector of claim 31, which is a recombinant expression vector.

33. A host cell containing the vector of claim 31.

34. A host cell containing the recombinant expression vector of claim 32.

35. A method for producing a polypeptide comprising culturing a host cell containing a nucleic acid molecule which encodes a polypeptide comprising the amino acid sequence of SEQ ID NO:3 or 6 in a suitable medium to thereby produce the polypeptide.

36. The method of claim 35, further comprising isolating the polypeptide from the medium or the host cell.

37. A method for producing a polypeptide comprising culturing a host cell containing a nucleic acid molecule which encodes a polypeptide comprising the amino acid sequence encoded by the human DNA insert of the plasmid deposited with ATCC® as Accession Number 98048 or 98049 in a suitable medium to thereby produce the polypeptide.

38. The method of claim 37, further comprising isolating the polypeptide from the medium or the host cell.

39. The nucleic acid molecule of claim 1, wherein the nucleotide sequence is at least 85% identical to the nucleotide sequence of SEQ ID NO:2.

40. The nucleic acid molecule of claim 39, wherein the nucleotide sequence is at least 90% identical to the nucleotide sequence of SEQ ID NO:2.

41. The nucleic acid molecule of claim 40, wherein the nucleotide sequence is at least 95% identical to the nucleotide sequence of SEQ ID NO:2.

42. The nucleic acid molecule of claim 41, which comprises the nucleotide sequence of SEQ ID NO:2.

43. An isolated nucleic acid molecule comprising a nucleotide sequence which at least 85% identical to the nucleotide sequence of SEQ ID NO:2.

44. The nucleic acid molecule of claim 1, wherein the nucleotide sequence is at least 95% identical to the nucleotide sequence of SEQ ID NO:5.

45. The nucleic acid molecule of claim 44, which comprises the nucleotide sequence of SEQ ID NO:5.

46. An isolated nucleic acid molecule comprising a nucleotide sequence which is at least 95% identical to the nucleotide sequence of SEQ ID NO:5.

47. An isolated nucleic acid molecule comprising a nucleotide sequence which is complementary to the nucleotide sequence of the nucleic acid molecule as in claim 39, 40, 41, 42, 43, 44, 45, or 46.

48. The nucleic acid molecule as in claim 39, 40, 41, 42, 43, 44, 45, or 46, which is genomic DNA.

49. The nucleic acid molecule as in claim 39, 40, 41, 42, 43, 44, 45, or 46, which is cDNA.

50. The nucleic acid molecule as in claim 39, 40, 41, 42, 43, 44, 45, or 46, which is RNA.

51. A vector comprising the nucleic acid molecule as in claim 39, 40, 41, 42, 43, 44, 45, or 46.

52. The vector of claim 51, which is a recombinant expression vector.

53. A host cell containing the vector of claim 51.

54. A host cell containing the recombinant expression vector of claim 52.

* * * * *